US008686110B2

(12) United States Patent
Colman et al.

(10) Patent No.: US 8,686,110 B2
(45) Date of Patent: Apr. 1, 2014

(54) THERAPEUTIC PRO-APOPTOTIC BH3-LIKE MOLECULES AND METHODS FOR GENERATING AND/OR SELECTING THE SAME

(75) Inventors: Peter Malcolm Colman, East Melbourne (AU); David Ching Siang Huang, North Fitzroy (AU); Erinna Faith Lee, Kew (AU); Walter Douglas Fairlie, Montmorency (AU)

(73) Assignee: The Walter and Eliza Hall Institute of Medical Research, Parkville, Victoria (AU)

( * ) Notice: Subject to any disclaimer, the term of this patent is extended or adjusted under 35 U.S.C. 154(b) by 777 days.

(21) Appl. No.: 11/993,829

(22) PCT Filed: Jun. 23, 2006

(86) PCT No.: PCT/AU2006/000888
§ 371 (c)(1),
(2), (4) Date: Sep. 24, 2008

(87) PCT Pub. No.: WO2006/135985
PCT Pub. Date: Dec. 28, 2006

(65) Prior Publication Data
US 2009/0048164 A1     Feb. 19, 2009

Related U.S. Application Data

(60) Provisional application No. 60/693,644, filed on Jun. 24, 2005.

(51) Int. Cl.
*C07K 5/00* (2006.01)
*C12N 15/00* (2006.01)

(52) U.S. Cl.
USPC ......................................... 530/300; 435/69.1

(58) Field of Classification Search
None
See application file for complete search history.

(56) References Cited

U.S. PATENT DOCUMENTS

| 2003/0060416 A1 | 3/2003 | Alnemri et al. |
| 2004/0171809 A1 | 9/2004 | Korsmeyer et al. |
| 2005/0064593 A1 | 3/2005 | Strasser et al. |

FOREIGN PATENT DOCUMENTS

| WO | WO 99/14321 A1 | 3/1999 |
| WO | WO 99/25832 A1 | 5/1999 |
| WO | WO 02/085899 A1 | 10/2002 |
| WO | WO2004050697 * | 6/2004 |
| WO | WO2004058804 * | 7/2004 |
| WO | WO 2006/074451 A2 | 7/2006 |

OTHER PUBLICATIONS

Bouilet et al, J Cell Science, vol. 115 p. 1567-1574, 2002.*
O'Connor et al EMBO vol. 17, p. 383-395, 1998.*
Egle et al, PNAS, vol. 101, p. 6164-6169, 2004.*
Sequence search result—Baell, 2010.*
Sequence search result—O'Connorr & NLM, 2010.*
Adams, J.M. 2003 "Ways of dying: multiple pathways to apoptosis" *Genes and Dev* 17:2481-2495.
Adams J.M and Cory, S. 1998 "The Bcl-2 protein family: arbiters of cell survival" *Science* 281:1322-1326.
Adams, J.M. et al. 1985 "The c-myc oncogene driven by immunoglobulin enhancers induces lymphoid malignancy in transgenic mice" *Nature* 318:533-538.
Akimaru, K. et al. 1995 "Formulation and antitumor efficacy of liposomal-caprylated-TNF-SAM2" *Cytokines Mol Ther* 1:197-210.
Alving, C.R. et al. 1995 "Liposomes as carriers of peptide antigens: induction of antibodies and cytotoxic T lymphocytes to conjugated and unconjugated peptides" *Immunological Rev* 145:5-31.
Bleicher, K.H. et al 2003 "Hit and Lead Generation: Beyond High-throughput screening" *Nat Rev Drug Discov* 2:369-378.
Chen et al. 2005 "Differnetial targeting of prosurvival Bcl-2 proteins by their BH3-only ligands allows complementary apoptotic function" *Mol Cell* 17:393-403.
Chittenden, T. et al. 1995 "A conserved domain in Bak, distinct from BH1 and BH2, mediates cell death and protein binding functions" *The EMBO J* 14:5589-5596.
Choi et al. 1995 A novel Bcl-2 related gene, Bfl-1, is overexpressed in stomach cancer and preferentially expressed in bone marrow: *Oncogene* 11:1693-1698.
Cory, S and Adams, J.M. et al. 2002 "The Bcl2 family: regulators of the cellular life-or death switch" *Nat Rev Cancer* 2:647-656.
Cory et al. 2003 "The Bcl-2 family: roles in cell survival and oncogenesis" *Oncogene* 22:8590-8607.
Cosulich, S.C. et al. 1997 "Regulation of apoptosis by BH3 domains in a cell-free system" *Current Biology* 7:913-920.
Danial, N.N. and Korsmeyer, S.J. 2004 "Cell Death: Critical control points" *Cell* 116:205-219.
Day, C.L. et al. 1999 "Solution structure and mutagenesis of the caspase recruitment domain (CARD) from Apaf-1" *Cell Death and Differentiation* 6:1125-1132.
D'Sa-Eipper, C. et al. 1996 "bfl-1, a bcl-2 homologue, suppresses p53-induced apoptosis and exhibits potent cooperative transforming activity" *Cancer Res* 56:3879-3882.
Egleton, R.D. and Davis, T.P. 1997 "Bioavailability and transport of peptides and peptide drugs into the brain" *Peptides* 18:1431-1439.
Erickson, J. et al. 1990 "Design, activity, and 2.8 Å crystal structure of a $C_2$ symmetric inhibitor complexed to HIV-1 protease" *Science* 249:527-533.
Fairlie, W.D. et al. 2004 "Affinity maturation of leukemia inhibitory factor and conversion to potent antagonists of signaling" *J Biol Chem* 279:2125-2134.
Fairlie, W.D. et al. 2002 "A fusion protein system for the recombinant production of short disulfide-containing peptides" *Protein Expression and Purification* 26:171-178.

(Continued)

*Primary Examiner* — Lei Yao
(74) *Attorney, Agent, or Firm* — Knobbe Martens Olson & Bear, LLP

(57) ABSTRACT

The present invention relates generally to therapeutic molecules which are useful for modulating apoptosis in a target cell or cell population. More particularly, the present invention provides therapeutic agents which inhibit pro-survival molecules and which are capable of inducing or facilitating apoptosis of a target cell or cell population such as cancer cells. The present invention further provides methods for generating or selecting the therapeutic molecules and pharmaceutical compositions comprising the therapeutic molecules.

13 Claims, No Drawings

(56) References Cited

OTHER PUBLICATIONS

Fix, J.A. 1996 "Oral controlled release technology for peptides: status and future prospects" *Pharm Res* 13:1760-1764.
Glickman, J.F. et al. 2002 "A comparison of ALPHAScreen, TR-FRET, and TFR as assay methods for FXR nuclear receptors" *J Biomol Screen* 7:3-10.
Hajduk, P.J. et al. 1999 "High-throughput nuclear magnetic resonance-based screening" *J Med Chem* 42:2315-2317.
Hinds, M.G. et al. 2003 "The structure of Bcl-w reveals a role for the C-terminal residues in modulating biological activity" *EMBO Journal* 22:1497-1507.
Holinger, E.P. et al. 1999 "Bak BH3 peptides antagonize Bcl-$x_L$ function and induce apoptosis through cytochrome c-independent activation of caspases" *J Biol Chem* 274:13298-13304.
Huang, D.C.S and Strasser, A. 2000 "BH3-only proteins-essential initiators of apoptotic cell death" *Cell* 103:839-842.
Johnstone, R.W. et al. 2002 "Apoptosis: a link between cancer genetics and chemotherapy" *Cell* 108:153-164.
Kelekar, A. et al. 1997 "Bad is a BH3 domain-containing protein that forms an inactivating dimer with Bcl-$x_L$" *Molec and Cell Biol* 17:7040-7046.
Kunkel, T.A. et al. 1991 "Efficient site-directed mutagenesis using uracil-containing DNA" *Methods Enzymol* 204:125-139.
Kuntz, I.D. 1992 "Structure-based strategies for drug design and discovery" *Science* 257:1078-1082.
Langer, R. 1990 "New methods of drug delivery" *Science* 249:1527-1533.
Lugovskoy, A.A. et al. 2002 "A novel approach for characterizing protein ligand complexes: Molecular basis for specificity of small-molecule Bcl-2 inhibitors" *J Am Chem Soc* 124:1234-1240.
Patton, J. 1998 "Breathing life into protein drugs" *Nat Biotech* 16:141-143.
Pellecchia, M. et al. 2002 "NMR in drug discover" *Nat Rev Drug Discov* 1:211-219.
Petros, A.M. et al. 2000 "Rationale for Bcl-$x_L$/Bad peptide complex formation from structure, mutagenesis, and biophysical studies" *Protein Science* 9:2528-2534.
Print, C.G. et al. 1998 "Apoptosis regulator Bcl-w is essential for spermatogenesis but appears otherwise redundant" *Proc Natl Acad Sci USA* 95:12424-12431.
Putney, S.D. and Burke, P.A 1998 "Improving protein therapeutics with sustained-release formulations" *Nat Biotech* 16:153-157.
Samanen, J. et al. 1996 "Chemical approaches to improve the oral bioavailability of peptidergic molecules" *J Pharm Pharmacol* 48:119-135.
Sattler, M. et al. 1997 "Structure of Bcl-$x_L$-Bak peptide complex: Recognition between regulators of apoptosis" *Science* 175:983-986.
Sayani, A.P. and Chien, Y.W. 1996 "Systemic delivery of peptides and proteins across absorptive mucosae" *Crit Rev Ther Drug Carrier Syst* 13:85-184.
Sidhu, S.S. et al. 2000 "Phage display for selection of novel binding peptides" *Methods Enzymol* 328:333-363.
Strasser, A. et al. 1990 "Novel primitive lymphoid tumours induced in transgenic mice by cooperation between myc and bcl-2" *Nature* 348:331-333.
Suntres, S.E. and Shek, P.N. 1994 "Incorporation of α-tocopherol in liposomes promotes the retention of liposome-encapsulated glutathione in the rat lung" *J Pharm Pharmacol* 46:23-28.
Szoka, F. Jr. and Papahadjopoulos, D. 1980 "Comparative properties and methods of preparation of lipid vesicles (Liposomes)" *Ann Rev Biophys Bioeng* 9:467-508.
Van De Waterbeemd, H. and Gifford, E. 2003 "ADMET in silico modelling: towards prediction paradise?" *Nat Rev Drug Disc* 2:192-204.
Vaux, D.L. et al. 1988 "Bcl-2 gene promotes haemopoietic cell survival and cooperates with c-myc to immortalize pre-B cells" *Nature* 335:440-442.
Vutla, N.B. et al. 1996 "Transdermal Iontophoretic delivery of enkephalin formulated in liposomes" *J Pharm Sci* 85:5-8.

Wang, K. et al. 1998 "Mutagenesis of the BH3 domain of BAX identifies residues critical for dimerization and killing" *Molec Cell Biol* 18:6083-6089.
Wei, M.C. et al. 2001 "Proapoptotic BAX and BAK: A requisite gateway to mitochondrial dysfunction and death" *Science* 292:727-730.
Wells, J.A. 1991 "Systematic mutational analyses of protein-protein interfaces" *Methods Enzymol* 202:2699-2705.
Willis, S.N. et al. 2005 "Proapoptotic Bak is sequestered by Mcl-1 and Bcl-$x_L$, but not Bcl-2 until displaced by BH3-only proteins" *Genes and Development* 19:1294-1305.
Wilson-Annan, J. et al. 2003 "Proapoptotic BH3-only proteins trigger membrane integration of prosurvival Bcl-w and neutralize its activity" *Journal of Cell Biology* 162:877-888.
Wohnsland, F. et al. 2001 "High-throughput permeability pH profile and high-throughput alkane/water logP with artificial membranes" *J Med Chem* 44:923-930.
Woodle, M.C. et al. 1992 "Prolonged systemic delivery of peptide drugs by Ion-circulating liposomes: illustration with vasopressin in the Brattleboro Rat" *Pharm Res* 9:260-265.
Yan, C et al. 2000 "Overexpression of the Cell Death Suppressor Bcl-w in Ischemic Brain: Implications for a Neuroprotective Role via the Mitochondrial Pathway" *J Cereb Blood Flow Metab* 20:620-630.
Zalipsky, S. et al. 1995 "Peptide attachment to extremities of liposomal surface grafted PEG chains: preparation of the long-circulating form of laminin pentapeptide YIGSR" *Bioconjug Chem* 6:705-708.
Zhang, J.Y. 2002 "Apoptosis-based anticancer drugs" *Nat Rev Drug Discov* 1:101-102.
Aggarwal, B.B. 2003 "Signalling pathways of the TNF superfamily: a double-edged sword" *Nature Review Immunology* 3:745-756.
Alikhani, M. et al. 2005 "FOXO1 Functions as a Master Switch that Regulates Gene Expression Necessary for Tumor Necrosis Factor-inducted Fibroblast Apoptosis" *Journal of Biological Chemistry* 280(13):12096-12102.
Arch, R. H. et al. 1998 "Tumor necrosis factor receptor-associated factors (TRAFs)—a family of adapter proteins that regulates life and death" *Genes & Development* 12:2821-2830.
Atherton, E. and Sheppard, R.C. 1994 in *Synthetic Vaccines*, Bruce H. Nicholson ed., Chapter 9: "Peptide Synthesis", Blackwell Scientific Publications, London.
Bouillet, P. et al. 1999 "Proapoptotic Bcl-2 relative Bim required for Certain Apoptotic Responses, Leukocyte Homeostasis, and to Preclude Autoimmunity" *Science* 286:1735-1738.
Bunin, B.A., et al. 1994 "The combinatorial synthesis and chemical and biological evaluation of a 1,4-benzodiazepine library" *Proc. Natl. Acad. Sci. USA* 91:4708-4712.
Cartee, L. et al. 2002 "Synergistic Induction of Apoptosis in Human Myeloid Leukemia Cells by Phorbol 12-Myristate 13-Acetate and Flavopiridol Proceeds via Activation of Both the Intrinsic and Tumor Necrosis Factor-Mediated Extrinsic Cell Death Pathways" *Molecular Pharmacology* 61(6):1313-1321.
Chen, D. et al. 2004 "Caspase cleavage of Bim$_{El}$ triggers a positive feedback amplication of apoptotic signaling" *PNAS* 101(5):1235-1240.
Chinnaiyan, A.M. et al. 1996 "Signal transduction by DR3, a death domain-containing receptor related to TNFR-1 and CD95.(death receptor 3; tumor necrosis factor receptor-1)" *Science* 274(5289):990-993.
Cretney, E. et al. 2002 "Increased Susceptibility to Tumor Initiation and Metastasis in TNF-Related Apoptosis-Inducing Ligand-Deficient Mice" *J. Immunol* 168:1356-1361.
Daniel, S. et al. 2004 "A20 protects endothelial cells from TNF-, Fas-, and NK-mediated cell death by inhibiting caspase 8 activation" *Blood* 104(8):2376-2384.
DeWitt, S.H. et al. 1993 ""Diversomers": An Approach to nonpeptide, nonoligomeric chemical diversity" *Proc. Natl. Acad. Sci. USA* 90:6909-6913.
Fehrenbacher, N. et al. 2004 "Sensitization to the Lyosomal Cell Death Pathway upon Immortalization and Transformation" *Cancer Research* 64(15):5301-5310.

(56) References Cited

OTHER PUBLICATIONS

Galanos, C. et al. 1979 "Galactosamine-induced sensitization to the lethal effects of endotoxin" *Proc Natl Acad Sci USA* 76 (11):5939-5943.
Grell, M. et al. 1995 "The Transmembrane Form of Tumor Necrosis Factor is the Prime Activating Ligand of the 80 kDa Tumor Necrosis Factor Receptor" *Cell* 83:793-802.
Grivennikov, S. I. et al. 2005 "Distinct and Nonredundant In Vivo functions of the TNF Produced by T Cells and Macrophages/Neutrophils: Protective and Deleterious Effects" *Immunity* 22:93-104.
Huang, D.C.S. et al. 2000 "BH3-Only Proteins—Essential Initiators of Apoptotic Cell Death" *Cell* 103:839-842.
Kägi, D. et al. 1994 "Cytotoxicity mediated by T cells and natural killer cells is greatly impaired in perforin-deficient mice" *Nature* 369:31-37.
Kang, T.B. et al. 2004 "Caspase-8 Serves Both Apoptotic and Nonapoptotic Roles" *J Immunol* 173:2976-2984.
Körner, H. et al. 1997 "Distinct roles for lymphotoxin-α and tumor necrosis factor in organogenesis and spatial organization of lymphoid tissue" *Eur J Immunol* 27:2600-2609.
Kuroda, J. et al. 2006 "Bim and Bad mediate imatinib-induced killing of Bcr/Abl+ leukemic cells, and resistance due to their loss is overcome by a BH3 mimetic" *PNAS* 103(40) 14907-14912.
Küsters, S. et al. 1997 "In vivo evidence for a functional role of both tumor necrosis factor (TNF) receptors and transmembrane TNF in experimental hepatitis" *Eur J Immunol* 27:2870-2875.
Li, H. et al. 1998 "Cleavage of BID by Caspase 8 Mediates the Mitochondrial Damage in the Fas Pathway of Apoptosis" *Cell* 94:491-501.
Locksley, R.M. et al. 2001 "The TNF and TNF Receptor Superfamilies: Integrating Mammalian Biology" 104:487-501.
Luo, X. et al. 1998 "Bid, a BCl2 Interacting Protein, Mediates Cytochrome c Release from Mitochondria in Response to Activation of Cell Surface Death Receptors" *Cell* 94:481-490.
Nowak, M. et al. 2000 "LPS-induced liver injury in D-galactosamine-sensitized mice requires secreted TNF-α and the TNF-p55 receptor" *Am J Physiol Regulatory Integrative Comp Physiol* 278:R1202-R1209.
O'Reilly, L.A. et al. 2000 "The Proapoptotic BH3-Only Protein Bim Is Expressed in Hematopoietic, Epithelial, Neuronal, and Germ Cells" *Amerian Journal of Pathology* 157(2):449-461.
Pao, L. I. et la. 2005 "Functional Analysis of Granzyme M and Its Role in Immunity to Infection" *J Immunol* 175:3235-43.
Pfeffer, K. et al. 1993 "Mice deficient for the 55 kd tumor necrosis factor receptor are resistant to endotoxic shock, yet succumb to *L. monocytogenes* infection" *Cell* 73(3):457-467.
Puthalakath, H. et al. 1999 "The Proapoptotic Activity of the Bcl-2 Family Member Bim is Regulated by Interaction with the Dynein Motor Complex" *Molecular Cell* 3:287-296.
Puthalakath, H. et al. 2002 "Keeping killers on a tight leash: transcriptional and post-translational control of the pro-apoptotic activity of BH3-only proteins" *Cell Death Differ* 9(5):505-12.
Rothe, J. et al. 1993 "Mice lacking the tumour necrosis factor receptor 1 are resistant to TNF-mediated toxicity but highly susceptible to infection by *Listeria monocytogenes*" *Nature* 364:798-802.
Salmena, L. et al. 2003 "Essential role for caspase 8 in T-cell homeostasis and T-cell-mediated immunity" *Genes and Development* 17:883-895.
Tagawa, Y.I. et al. 1998 "Involvement of Fas/Fas ligand system-mediated apoptosis in the development of concanavalin A-induced hepatitis" *European Journal of Immunology* 28:4105-4113.
Tartaglia, L.A. et al. 1993 "Tumor necrosis factor's cytotoxic activity is signaled by the p55 TNF receptor" *Cell* 73(2):213-216.
Tiegs, G et al. 1992 "A T Cell-dependent Experimental Liver Injury in Mice Inducible by Concanavalin A" *J Clin Invest* 90:196-203.
Trautwein, C. et al. 1998 "Concanavalin A-Induced Liver Cell Damage: Activation of Intracellular Pathways Triggered by Tumor Necrosis Factor in Mice" *Gastroenterology* 114:1035-1045.
Wang, K. et al. 1996 "BID: a novel BH3 domain-only death agonist" *Genes and Development* 10:2859-2869.
Watanabe, Y. et al. 1996 "Concanavalin A Induces Perforin-Mediated But Not Fas-Mediated Hepatic Injury" *Hepatology* 24(3):702-710.
Yin, X.M. et al. 1999 "Bid-deficient mice are resistant to Fas-inducted hepatocellular apoptosis" *Nature* 400:886-891.
Zha, J. et al. 2000 "Postranslational N-Myristoylation of BID as a Molecular Switch for Targeting Mitochondria and Apoptosis" *Science* 290(5497):1761-1765.
Zheng, S.J. et al. 2004 "Critical roles of TRAIL in hepatic cell death and hepatic inflammation" *J Clin Invest* 113:58-64.
Adachi, M. et al. 2003 "Mutation of BAD within the BH3 domain impairs its phosphorylation-mediated regulation" *FEB Letters* 551:147-152.
Kuwana, T. et al. 2005 "BH3 Domains of BH3-Only Proteins Differentially Regulate Bax-Mediated Mitochondrial Membrane Permeabilization Both Directly and Indirectly" *Molecular Cell* 17:525-535.
Lee, E. F. et al. 2008 "A novel BH3 ligand that selectively targets Mcl-1 reveals that apoptosis can proceed without Mcl-1 degradation" *Journal of Cell Biology* 180(2): 341-355.
Letai, A. et al. 2002 "Distinct BH3 domains either sensitize or activate mitochondrial apoptosis, serving as prototype cancer therapeutics" *Cancer Cell* 2:183-192.
Oltersforf, T. et al. 2005 "An inhibitor of Bcl-2 family proteins induces regression of solid tumours" *Nature* 435:677-681.
Supplemental European Search Report dated Apr. 21, 2009 for European Application No. EP06752632.
Heibein, J.A. et al. 2000 "Granzyme B-mediated cytochrome c release is regulated by the Bcl-2 family members Bid and Bax" *J Exp. Med.* 192: 1391-1401.

\* cited by examiner

```
                          SEQUENCE LISTING

<160> NUMBER OF SEQ ID NOS: 11

<210> SEQ ID NO 1
<211> LENGTH: 26
<212> TYPE: PRT
<213> ORGANISM: Homo sapiens

<400> SEQUENCE: 1

Asp Met Arg Pro Glu Ile Trp Ile Ala Gln Glu Leu Arg Arg Ile Gly
1               5                   10                  15

Asp Glu Phe Asn Ala Tyr Tyr Ala Arg Arg
            20                  25

<210> SEQ ID NO 2
<211> LENGTH: 26
<212> TYPE: PRT
<213> ORGANISM: Homo sapiens

<400> SEQUENCE: 2

Glu Glu Gln Trp Ala Arg Glu Ile Gly Ala Gln Leu Arg Arg Met Ala
1               5                   10                  15

Asp Asp Leu Asn Ala Gln Tyr Glu Arg Arg
            20                  25

<210> SEQ ID NO 3
<211> LENGTH: 24
<212> TYPE: PRT
<213> ORGANISM: Homo sapiens

<400> SEQUENCE: 3

His Arg Ala Glu Val Gln Ile Ala Arg Lys Leu Gln Cys Ile Ala Asp
1               5                   10                  15

Gln Phe His Arg Leu His Thr Gln
            20

<210> SEQ ID NO 4
<211> LENGTH: 26
<212> TYPE: PRT
<213> ORGANISM: Homo sapiens

<400> SEQUENCE: 4

Asn Leu Trp Ala Ala Gln Arg Tyr Gly Arg Glu Leu Arg Arg Met Ser
1               5                   10                  15

Asp Glu Phe Val Asp Ser Phe Lys Lys Gly
            20                  25

<210> SEQ ID NO 5
```

```
<211> LENGTH: 25
<212> TYPE: PRT
<213> ORGANISM: Homo sapiens

<400> SEQUENCE: 5

Met Glu Gly Ser Asp Ala Leu Ala Leu Arg Leu Ala Cys Ile Gly Asp
1               5                   10                  15

Glu Met Asp Val Ser Leu Arg Ala Pro
            20                  25

<210> SEQ ID NO 6
<211> LENGTH: 26
<212> TYPE: PRT
<213> ORGANISM: Homo sapiens

<400> SEQUENCE: 6

Arg Ser Ser Ala Ala Gln Leu Thr Ala Ala Arg Leu Lys Ala Ile Gly
1               5                   10                  15

Asp Glu Leu His Gln Arg Thr Met Trp Arg
            20                  25

<210> SEQ ID NO 7
<211> LENGTH: 26
<212> TYPE: PRT
<213> ORGANISM: Homo sapiens

<400> SEQUENCE: 7

Gln Glu Asp Ile Ile Arg Asn Ile Ala Arg His Leu Ala Gln Val Gly
1               5                   10                  15

Asp Ser Met Asp Arg Ser Ile Pro Pro Gly
            20                  25

<210> SEQ ID NO 8
<211> LENGTH: 26
<212> TYPE: PRT
<213> ORGANISM: Homo sapiens

<400> SEQUENCE: 8

Pro Ala Glu Leu Glu Val Glu Cys Ala Thr Gln Leu Arg Arg Phe Gly
1               5                   10                  15

Asp Lys Leu Asn Phe Arg Gln Lys Leu Leu
            20                  25

<210> SEQ ID NO 9
<211> LENGTH: 26
<212> TYPE: PRT
<213> ORGANISM: Mus musculus

<400> SEQUENCE: 9

Arg Ala Glu Leu Pro Pro Glu Phe Ala Ala Gln Leu Arg Lys Ile Gly
1               5                   10                  15

Asp Lys Val Tyr Cys Thr Trp Ser Ala Pro
            20                  25

<210> SEQ ID NO 10
<211> LENGTH: 26
<212> TYPE: PRT
<213> ORGANISM: Mus musculus

<400> SEQUENCE: 10

Pro Ala Asp Leu Lys Asp Glu Cys Ala Gln Leu Arg Arg Ile Gly Asp
1               5                   10                  15

Lys Val Asn Leu Arg Gln Lys Leu Leu Asn
```

```
<210> SEQ ID NO 11
<211> LENGTH: 26
<212> TYPE: PRT
<213> ORGANISM: Homo sapiens

<400> SEQUENCE: 11

Pro Ser Ser Thr Met Gly Gln Val Gly Arg Gln Leu Ala Ile Ile Gly
1               5                   10                  15

Asp Asp Ile Asn Arg Arg Tyr Asp Ser Glu
            20                  25
```

US 8,686,110 B2

THERAPEUTIC PRO-APOPTOTIC BH3-LIKE MOLECULES AND METHODS FOR GENERATING AND/OR SELECTING THE SAME

This application is U.S. National Phase of International Application PCT/AU2006/000888, filed Jun. 23, 2006 designating the U.S., and published in English as WO 2006/135985 on Dec. 28, 2006, which claims priority to U.S. Provisional Application No. 60/693,644 filed Jun. 24, 2005.

BACKGROUND OF THE INVENTION

1. Field of the Invention

The present invention relates generally to therapeutic molecules which are useful for modulating apoptosis in a target cell or cell population. More particularly, the present invention provides therapeutic agents which inhibit pro-survival molecules and which are capable of inducing or facilitates apoptosis of a target cell or cell population such as cancer cells. The present invention further provides methods for generating or selecting the therapeutic molecules and pharmaceutical compositions comprising the therapeutic molecules.

2. Description of the Prior Art

Reference to any prior art in this specification is not, and should not be taken as, an acknowledgment or any form of suggestion that this prior art forms part of the common general knowledge in any country.

Bibliographic details of references provided in this document are listed at the end of the specification.

Cancer is the second leading cause of death in the developed world. Apart from the suffering it causes to patients and their families it is also one of the most expensive diseases to treat (Zhang, *Nat Rev Drug Discov* 1:101-102, 2002). Accordingly, notwithstanding the toll on human life, if both treatment costs and the cost of reduced economic productivity are considered, the total annual economic burden to society is expected to be in the order of US$200-500 billion by 2010.

Perturbation of programmed cell death (apoptosis) is a central step in the development of many major diseases including cancer. One family of critical regulators of apoptosis is the Bcl-2 protein family. Studies have shown that Bcl-2 overexpression, enforced in human follicular lymphoma, inhibits apoptosis and contributes to tumorigenesis (Vaux et al., *Nature* 335:440-442, 1988; and Strasser et al., *Nature* 348:331-333, 1990). Bcl-2 overexpression has also been noted in up to 90% of breast, colonic and prostatic cancers (Zhang, 2002, Supra), which represent some of the most common cancers. Pro-survival relatives of Bcl-2 are also overexpressed in many tumors. Indeed, impaired apoptosis is now accepted as a central step in the development of most forms of malignancy (Cory et al., *Nat Rev Cancer* 2:647-656, 2002).

Impaired apoptosis is also a major impediment to the efficacy of cytotoxic cancer therapy (Cory et al., 2002, Supra; Johnstone et al., *Cell* 108:153-164, 2002). Most cytotoxic agents, including many chemotherapeutic drugs and radiation, indirectly trigger apoptosis through molecules such as the tumor suppressor p53 (Cory et al., 2002, Supra). In most tumors, however, the p53 pathway is inactivated, preventing the signals to initiate apoptosis. Hence, either loss of p53 function or overexpression of Bcl-2 can provoke chemoresistance, a common cause for treatment failure.

Those members of the Bcl-2 protein family that promote cell survival, including mammalian Bcl-2, Bcl-$x_L$, Bcl-w, Mcl-1 and A1, contain three or four BH (Bcl-2 homology) regions of sequence similarity, and function until neutralized by their BH3-only relatives. These pro-apoptotic antagonists, which include mammalian Bim, Puma, Bmf, Bad, Bik, Hrk, Bid and Noxa, are related to each other and the wider family only by the short BH3 domain (Huang and Strasser, *Cell* 103:839-842, 2000). In contrast, Bax and Bak, a sub-group of pro-apoptotic family members, share three BH domains with Bcl-2 and have an essential downstream role, probably in permeabilization of intracellular membranes (Wei et al., *Science* 292:727-730, 2001).

The BH3-only proteins monitor cellular well-being and damage signals trigger their binding to pro-survival Bcl-2-like proteins, thereby initiating cell death (Cory et al., *Oncogene* 22:8590-8607, 2003; Huang and Strasser, 2000, Supra). Their differential activation, induced by transcriptional cues (e.g. Bim, Puma, Noxa) or various post-translational mechanisms (e.g. Bim, Bmf, Bad, Bid), imparts some signaling specificity (Puthalakath et al., *Cell Death Differ* 9:505-512, 2002). Once activated, however, the various BH3-only proteins are generally thought to function similarly by targeting all the pro-survival Bcl-2-like proteins (Adams et al., *Genes Dev* 17:2481-2495, 2003; Cory et al. 2003 supra; Huang and Strasser, 2000, Supra). Until recently their interactions have not been systematically characterized, and the few quantitative studies were confined to Bcl-$x_L$ or Bcl-2 (Letai et al., *Cancer Cell* 2:183-192, 2002; Petros et al., 2000, Supra; Sattler et al., 1997, Supra). A thorough study has now been published (Chen et al. *Mol Cell* 17:393-403, 2005) revealing that some of the BH3 only proteins are promiscuous binders and others are more selective. Establishing whether the diverse BH3-only proteins and pro-survival family members interact selectively or promiscuously is important for clarifying how cell death initiates (Adams, 2003, Supra; Cory et al., 2003, Supra; Danial and Korsmeyer, *Cell* 116:205-219, 2004) and is very pertinent to current efforts to develop compounds that mimic the action of BH3-only proteins as novel anti-cancer agents.

In light of the requirement for less toxic and better targeted anti-cancer therapies, there is a clear need for the identification of molecules which interact with Bcl-2-like proteins to inhibit their pro-survival function.

SUMMARY OF THE INVENTION

The present invention relates to molecules useful for modulating apoptosis of a cell or cell population. Specifically, the present invention provides antagonists of pro-survival molecules, and in particular antagonists of one or more members of the pro-survival Bcl-2 family of proteins.

The generation and/or selection of the subject pro-survival Bcl-2 interaction molecules is based on the identification of amino acid residues within BH3-only pro-apoptotic proteins which are essential for binding to occur between a BH3 domain from a BH3-only protein and a pro-survival Bcl-2 protein.

The BH3-only proteins are distinguishable functionally with respect to the spectrum of pro-survival Bcl-2 proteins to which they interact. By identifying the amino acids which are essential for binding to occur between a specific BH3-only protein and a specific pro-survival Bcl-2 protein, antagonists are generated or selected which specifically interact with a pro-survival Bcl-2 protein and inhibit its function. Contact of these antagonists with a target cell or cell population, such as a cancer, prevents the activity of the pro-survival Bcl-2 protein, thereby inducing apoptosis in the target cell or target cell population. Alternatively, identification of these targets leads to the generation of molecules useful in inhibiting the interaction of apoptotic molecules and pro-survival molecules hence leading to promotion of cell survival. Such molecules are useful in the treatment of degenerative diseases.

One embodiment of the present invention contemplates, therefore, agents which antagonize specific pro-survival Bcl-2 protein enabling apoptosis to be induced in selected types of cells or cell populations such as, but not limited to, cancer cells or cells associated with hyperproliferative diseases.

In particular, the present invention contemplates a method for generating an antagonist of a pro-survival Bcl-2 family member, the method comprising the steps of;
 a. mutating one or more amino acid residues of a BH3 domain from a BH3-only pro-apoptotic protein;
 b. contacting the mutated BH3 domain with the pro-survival Bcl-2 family member;
 c. detecting the presence of binding between the mutated BH3 domain and the pro-survival Bcl-2 family member, thereby identifying amino acid residues in the BH3 domain of the pro-apoptotic protein associated with a binding interaction between the BH3 domain and the pro-survival Bcl-2 family member; and
 d. generating an antagonist which mimics the wild-type BH3 domain at the residues essential for binding to occur between the BH3 domain and the Bcl-2 protein.

"Detecting" in part c) above includes indirect detection via the effects of the pro-survival protein or pro-apoptotic protein as well as direct detection of binding.

Conveniently, the antagonist is a peptide which binds to the pro-survival protein and inhibits its function. Hence, in one particular embodiment the antagonist is a peptide antagonist or peptide mimetic based on a modified BH3-only pro-apoptotic protein.

The antagonists of the present invention may be specific for one or more pro-survival molecules, including but not limited to Bcl-2, Bcl-$x_L$, Bcl-w, Mcl-1 or A1. The identification of the antagonists is made via the mutation of resides within pro-apoptotic proteins such as, without being limited to, one or more of Noxa, Bim, Puma, Bmf, Bad, Bik, Hrk and Bid.

| | |
|---|---|
| Bim: | D1A, M2A, R3A, P4A, E5A, I6A, W7A, I8A, A9E, Q10A, E11A, L12A, R13A, R14A, I15A, G16E, D17A, E18A, F19A, N20A, A21E, Y22A, Y23A, A24E, R25A and R26A; |
| Bad: | N1A, L2A, W3A, A4E, A5E, Q6A, R7A, Y8A, G9E, R10A, E11A, L12A, R13A, R14A, M15A, S16E, D17A, E18A, F19A, V20A, D21A, S22A, F23A, K24A, K25A and G26E; |
| Bid: | Q1A, E2A, D3A, I4A, I5A, R6A, N7A, I8A, A9E, R10A, H11A, L12A, A13E, Q14A, V15A, G16E, D17A, S18A, M19A, D20A, R21A, S22A, I23A, P24A, P25A and G26E; |
| mNoxaA: | R1A, A2E, E3A, L4A, P5A, P6A, E7A, F8A, A9E, A10E, Q11A, L12A, R13A, K14A, I15A, G16E, D17A, K18A, V19A, Y20A, C21A, T22A, W23A, S24A, A25E and D26A; |
| Bak: | P1A, S2A, S3A, T4A, M5A, G6E, Q7A, V8A, G9E, R10A, Q11A, L12A, A13E, I14A, I15A, G16E, D17A, D18A, I19A, N20A, R21A, R22A, Y23A, D24A, S25A and E26A. |

In the above lists of mutations "XnY" represents a substitution of amino acid residue X for amino acid residue Y at residue number n. The residue number correspond to the amino acid sequence of the BH3 domain. For any given pro-apoptotic molecule, one or more mutations may exist.

Antagonists of the pro-survival Bcl-2 family member may be generated by methods such as, but not limited to, in silico screening, high throughput chemical screening, functional based assays or structure-activity relationships.

In yet another embodiment, the antagonists of the present invention are conveniently provided in a medicament form such as a pharmaceutical composition.

The antagonists of the present invention are particularly useful in treating subjects with cancer or a hyperproliferative disease or the propensity to develop cancer or a hyperproliferative disease.

Pro-survival molecules of the present invention, include without being limited to members of the Bc-2 pro-survival family of proteins, including, without being limited to, Bcl-2, Bcl-$x_L$, Bcl-w, Mcl-1 and A1.

A summary of sequence identifiers used throughout the subject specification is provided in Table 1.

TABLE 1

Summary of Sequence Identifiers

| SEQUENCE ID NO: | DESCRIPTION |
|---|---|
| 1 | BH3 domain of BIM: DMRPEIWIAQELRRIGDEFNAYYARR |
| 2 | BH3 domain of Puma: EEQWAREIGAQLRRMADDLNAQYERR |
| 3 | BH3 domain of mBmf: -HRAEVQIARKLQCIADQFHRLHTQ- |
| 4 | BH3 domain of Bad: NLWAAQRYGRELRRMSDEFVDSFKKG |
| 5 | BH3 domain of Bik: -MEGSDALALRLACIGDEMDVSLRAP |
| 6 | BH3 domain of Hrk: RSSAAQLTAARLKAIGDELHQRTMWR |
| 7 | BH3 domain of Bid: QEDIIRNIARHLAQVGDSMDRSIPPG |
| 8 | BH3 domain of Noxa: PAELEVECATQLRRFGDKLNFRQKLL |
| 9 | BH3 domain of mNoxaA: RAELPPEFAAQLRKIGDKVYCTWSAP |
| 10 | BH3 domain of mNoxaB: -PADLKDECAQLRRIGDKVNLRQKLLN |
| 11 | BH3 domain of Bak: PSSTMGQVGRQLAIIGDDINRRYDSE |

A "-" at the beginning or end of a sequence denotes a deletion of an amino acid residue.

In a particular embodiment, the antagonists of the present invention are derived from a pro-apoptotic protein having a BH3-only domain sequence selected from SEQ ID NOs:1 through 10 wherein the BH3-only domain carries one or more amino acid substitutions, deletions or additions at one or more of amino acid positions and/or at a N- and/or C-terminal end portion.

Particular mutants of pro-apoptotic molecules include a mutation selected from:

DETAILED DESCRIPTION OF THE INVENTION

Before describing the present invention in detail, it is to be understood that unless otherwise indicated, the subject invention is not limited to specific formulations of components, manufacturing methods, dosage or diagnostic regimes, or the like. It is also to be understood that the terminology used herein is for the purpose of describing particular embodiments only and is not intended to be limiting.

The singular forms "a", "an" and "the" include plural aspects unless the context clearly dictates otherwise. Thus, for example, reference to "a BH3-only protein" includes a single BH3-only protein as well as two or more BH3-only proteins; reference to "an agent" includes a single agent, as well as two or more agents; reference to "the formulation" includes a single formulation or multiple formulations; and so forth.

All scientific citations, patents, patent applications and manufacturer's technical specifications referred to hereinafter are incorporated herein by reference in their entirety.

A "-" at the beginning or end of a sequence denotes a deletion of an amino acid residue.

Mutations in the BH3 domain are represented as "X n Y" wherein amino acid residue X replaces amino acid residue Y at position number.

In describing and claiming the present invention, the following terminology is used in accordance with the definitions set forth below.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The terms "agent", "compound", "pharmacologically active agent", "medicament" and "active" may be used interchangeably herein to refer to a substance that induces a desired pharmacological and/or physiological effect. The terms also encompass pharmaceutically acceptable and pharmacologically active forms thereof, including but not limited to salts, esters, amides, prodrugs, active metabolites, analogs and the like. The desired effect is, in one embodiment the inhibition or antagonism of a pro-survival molecule thereby inducing cellular apoptosis. In another embodiment, the desired effect is to promote cell survival by antagonising pro-apoptotic molecules.

Reference to an "agent", "pharmacologically active agent", and "medicament" may include combinations of two or more of such substances, such as for example, two or more pro-survival antagonists. A "combination" also includes multi-part combinations such as a two-part composition where the agents are provided separately and given or dispensed separately or admixed together prior to dispensation. For example, a multi-part pharmaceutical pack may have two or more antagonists to two or more pro-survival proteins separately maintained. Combination therapy involving the use of a pro-survival antagonist and an anti-cancer agent (i.e. a chemotherapeutic agent) also forms part of the present invention.

The terms "effective amount" and "therapeutically effective amount" as used herein mean a sufficient amount of an agent which provides the desired therapeutic or physiological effect or outcome, such as inhibiting the activity of a pro-survival protein or inducing apoptosis of target cells. In addition, the effect may be an amelioration of the symptoms of a cellular disorder such as cancer. Then again, the desired effect may be the promotion of cell survival such as in the case of a degenerative disease. Undesirable effects, e.g. side effects, are sometimes manifested along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an antagonist of a pro-survival protein to function may be readily ascertained in vitro or in an animal model. With respect to the latter, one of ordinary skill in the art would be able to determine the required amounts based on such factors as the animal's, the severity of the animal's symptoms, and the particular composition or route of administration selected. This information could then be extrapolated to larger animals such as a human.

Insofar as one embodiment of the present invention relates to the use of proteins or peptides, the effective amount includes from about 10 μg/kg body weight to 20 mg/kg body weight of antibody such as 10, 20, 30, 40, 50, 60, 70, 80, 90, 100 μg/kg body weight, 100, 200, 300, 400, 500, 600, 700, 800, 900, 1000 μg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

A "pharmaceutically acceptable" carrier and/or diluent is a pharmaceutical vehicle comprised of a material that is not biologically or otherwise undesirable, i.e. the material may be administered to a subject along with the selected active agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt, ester, amide, prodrug or derivative of a compound as provided herein is a salt, ester, amide, prodrug or derivative that is not biologically or otherwise undesirable.

The terms "treating" and "treatment" as used herein refer to therapeutic treatment and prophylactic or preventative measures. For example, treatment may result in a reduction in severity and/or the frequency of symptoms of cancer, the elimination of symptoms and/or underlying cause of cancer, the prevention of the occurrence of symptoms of cancer and/or their underlying cause and improvement or remediation or amelioration of damage following cancer. Hence, the treatment may not result in a "cure" but rather an amelioration of symptoms. In addition, the treatment may not be of the primary cancer but secondary or metastasising cancers.

The terms "condition" and "disease" are used interchangeably throughout the subject specification.

A "subject" as used herein refers to an animal, preferably a mammal and more preferably a human who can benefit from the pharmaceutical compositions and methods of the present invention. There is no limitation on the type of animal that could benefit from the presently described pharmaceutical compositions and methods. A subject regardless of whether a human or non-human animal may be referred to as an individual, patient, animal, host or recipient as well as subject. The compounds and methods of the present invention have applications in human medicine and veterinary medicine.

Preferred mammals are humans, laboratory test animals and animals involved in the racing and endurance industries. Examples of laboratory test animals include mice, rats, rabbits, guinea pigs, hamsters, cats and dogs. Examples of animals in the racing and endurance industries include horses, dogs, cows and camels.

The present invention contemplates methods for generating antagonists of pro-survival proteins. The antagonists induce or promote apoptosis. The antagonists of the present invention are generated based on the identification of amino acid residues in pro-apoptotic molecules which are involved in the binding between members of the BH3-only family of pro-apoptotic proteins and members of the pro-survival family of Bcl-2 proteins.

The present invention relates therefore to molecules useful for modulating apoptosis of a cell or cell population. Specifically, the present invention relates in one embodiment to antagonists of pro-survival members of Bcl-2 family of proteins.

Reference herein to "apoptosis" means a form of cell death in which a programmed sequence of invents leads to the death and elimination of cells. Apoptotic cells undergo distinct morphological changes. Hallmarks of apoptosis include cell shrinkage, nuclear and cytoplasmic condensation, and alterations in plasma membrane topology. Biochemically, apoptotic cells are characterized by increased intracellular calcium concentration, fragmentation of chromosomal DNA, and expression of novel cell surface components.

Accordingly, in one embodiment of the present invention, antagonists are made to one or more members of the Bcl-2 family of proteins, enabling apoptosis to be induced in selected cells or cellular populations, such as, but not limited to cancer cells, and cells undergoing undesirable hyperproliferation.

Reference herein to "cancer cells" means cells that exhibit abnormal growth and which tends to proliferate in an uncontrolled way and, in some cases lead to tumors and/or metastases. Cancers contemplated for treatment using the antagonists of the present invention include, without being limited to, ABL1 protooncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and cns tumors, breast cancer, cns tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofibrosarcoma-protuberans, desmoplastic-small-round-cell-tumor, ductal carcinoma, endocrine cancers, endometrial cancer, ependymoma, esophageal cancer, ewing's sarcoma, extra-hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, rothmund-thomson syndrome, salivary gland cancer, sarcoma, schwannoma, sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

Cancers that are particular targets of the present invention are those which produce an excess amount of a Bcl-2 protein or pro-survival protein relative and/or reduced amounts of a pro-apoptotic molecule which inhibits a Bcl-2 family member.

In accordance with the present invention, pro-survival molecules include, without being limited to, Bcl-2 proteins. The Bcl-2 family of proteins, as well as other cytoplasmic proteins, are key regulators of apoptosis. There are currently identified at least 15 Bcl-2 family members within 3 subfamilies. These proteins have been identified in mammalian cells and in viruses, and each possesses at least one of four Bcl-2 homology domains (BH1 to BH4), which are highly conserved. Bcl-2 family proteins contain the BH1 and BH2 domains, which are found in members of the pro-survival subfamily, while those proteins which are most similar to Bcl-2 have all four conserved domains, enabling inhibition of apoptosis following encounters with a variety of cytotoxic challenges. Members of the pro-survival subfamily include Bcl-2, Bcl-$X_L$, Bcl-w, Mcl-1, and A1 in mammals; NF-13 (chicken); CED-9 (*Caenorhabditis elegans*); and viral proteins BHRF1, LMW5-BL, ORF16, KS-Bcl-2, and E1B-19K. The BH3 domain is essential for the function of pro-apoptosis subfamily proteins. The two pro-apoptosis subfamilies, Bax and BH3, include Bax, Bak, and Bok (also called Mtd); and Bik, Blk, Hrk, BNIP3, Bim$^L$, Bad, Bid, and Egl-1 (*C. elegans*), respectively. Members of the Bax subfamily contain the BH1, BH2, and BH3 domains, and resemble Bcl-2 rather closely. In contrast, members of the BH3 subfamily have only the 9-16 residue BH3 domain, being otherwise unrelated to any known protein, and only Bik and Blk share sequence similarity. The proteins of the two pro-apoptosis subfamilies may be the antagonists of pro-survival subfamily proteins. This is illustrated in *C. elegans* where Egl-1, which is required for apoptosis, binds to and acts via CED-9 (for review, see Adams, J. M. and S. Cory *Science* 281:1322-1326, 1998).

Heterodimerization between pro-apoptosis and anti-apoptosis subfamily proteins has a titrating effect on the functions of these protein subfamilies, which suggests that relative concentrations of the members of each subfamily may act to regulate apoptosis.

The Bcl-2 protein has 2 isoforms, alpha and beta, which are formed by alternative splicing. It forms homodimers and heterodimers with Bax and Bak proteins and the Bcl-$X_L$ isoform Bcl-$X_S$. Heterodimerization with Bax requires intact BH1 and BH2 domains, and is necessary for pro-survival activity. The BH4 domain seems to be involved in pro-survival activity as well. Bcl-2 is located within the inner and outer mitochondrial membranes, as well as within the nuclear envelope and endoplasmic reticulum, and is expressed in a variety of tissues. Its involvement in follicular lymphoma (type II chronic lymphatic leukemia) is seen in a chromosomal translocation T(14;18) (q32;q21) and involves immunoglobulin gene regions.

The Bcl-$X_L$ protein is a dominant regulator of apoptotic cell death. Alternative splicing results in three isoforms, Bcl-xB, a long isoform, and a short isoform. The long isoform exhibits cell death repressor activity, while the short isoform promotes apoptosis. Bcl-$X_L$ forms heterodimers with Bax and Bak, although heterodimerization with Bax does not seem to be necessary for pro-survival (anti-apoptosis) activity. Bcl-Xs forms heterodimers with Bcl-2. Bcl-x is found in mitochondrial membranes and the perinuclear envelope. Bcl-$X_S$ is expressed at high levels in developing lymphocytes and other cells undergoing a high rate of turnover. Bcl-$X_L$ is found in adult brain and in other tissues' long-lived post-mitotic cells. As with Bcl-2, the BH1, BH2, and BH4 domains are involved in pro-survival activity.

The Bcl-w protein is found within the cytoplasm of almost all myeloid cell lines and in numerous tissues, with the highest levels of expression in brain, colon, and salivary gland. This protein is expressed in low levels in testis, liver, heart, stomach, skeletal muscle, and placenta, and a few lymphoid cell lines. Bcl-w contains the BH1, BH2, and BH4 domains, all of which are needed for its cell survival promotion activity. Although mice in which Bcl-w gene function was disrupted by homologous recombination were viable, healthy, and normal in appearance, and adult females had normal reproductive function, the adult males were infertile. In these males, the initial, prepuberty stage of spermatogenesis was largely unaffected and the testes developed normally. However, the seminiferous tubules were disorganized, contained numerous apoptotic cells, and were incapable of producing mature sperm. This mouse model may be applicable in some cases of human male sterility and suggests that alteration of programmed cell death in the testes may be useful in modulating fertility (Print et al. *Proc Natl Acad Sci USA* 95:12424-12431, 1998).

Studies in rat ischemic brain found Bcl-w to be overexpressed relative to its normal low constitutive level of expression in nonischemic brain. Furthermore, in vitro studies to examine the mechanism of action of Bcl-w revealed that isolated rat brain mitochondria were unable to respond to an addition of recombinant Bax or high concentrations of calcium when Bcl-w was also present. The normal response would be the release of cytochrome c from the mitochondria. Additionally, recombinant Bcl-w protein was found to inhibit calcium-induced loss of mitochondrial transmembrane potential, which is indicative of permeability transition. Together these findings suggest that Bcl-w may be a neuroprotectant against ischemic neuronal death and may achieve this protection via the mitochondrial death-regulatory pathway (Yan et al. *J Cereb Blood Flow Metab* 20:620-630, 2000).

The Bfl-1 gene is an additional member of the Bcl-2 family, and is also a suppressor of apoptosis. The Bfl-1 protein has 175 amino acids, and contains the BH1, BH2, and BH3 conserved domains found in Bcl-2 family members. It also contains a Gln-rich NH2-terminal region and lacks aBH domain 1, unlike other Bcl-2 family members. The mouse A1 protein shares high sequence homology with Bfl-1 and has the 3 conserved domains found in Bfl-1. Apoptosis induced by the p53 tumor suppressor protein is suppressed by Bfl-1, similar to the action of Bcl-2, Bcl-xL, and EBV-BHRF1 (D'Sa-Eipper, C. et al. *Cancer Res*. 56:3879-3882, 1996). Bfl-1 is found intracellularly, with the highest expression in the hematopoietic compartment, i.e. blood, spleen, and bone marrow; moderate expression in lung, small intestine, and testis; and minimal expression in other tissues. It is also found in vascular smooth muscle cells and hematopoietic malignancies. A correlation has been noted between the expression level of Bfl-1 and the development of stomach cancer, suggesting that the Bfl-1 protein is involved in the development of stomach cancer, either in the promotion of cancerous cell survival or in cancer (Choi et al. *Oncogene* 11:1693-1698, 1995). In certain embodiments, the pro-survival molecules include, without being limited to, Bcl-2, Bcl-$x_L$, Bcl-w, Mcl-1 and A1.

The pro-apoptotic molecules contemplated by the present invention include, without being limited to, members of the BH3-only family of proteins. In some embodiments, the BH3-only proteins include, without being limited to, Noxa, Bim, Puma, Bmf, Bad, Bik, Hrk and Bid.

The present invention, provides antagonists which can selectively bind to one or more of Bcl-2, Bcl-$x_L$, Bcl-w, Mcl-1 and A1, thereby resulting in apoptosis of the target cell or cell population.

Accordingly, the present invention provides a method of generating an antagonist of a pro-survival Bcl-2 family member, the method comprising the steps of;
   a. mutating one or more amino acid residues of a BH3 domain from a BH3-only pro-apoptotic protein;
   b. contacting the mutated BH3 domain with the pro-survival Bcl-2 family member;
   c. detecting the presence or absence of binding between the mutated BH3 domain and the pro-survival Bcl-2 family member, thereby identifying amino acid residues in the BH3 domain of the pro-apoptotic protein associated with a binding interaction the BH3 domain and the pro-survival Bcl-2 family member; and
   d. generating an antagonist which mimics the wild-type BH3 domain at the residues essential for binding to occur between the BH3 domain and the Bcl-2 protein.

Reference herein to "mutating" refers to the substitution or deletion of one or more residues within the BH3 domain sequence. Examples of which are disclosed in SEQ ID NOs: 1-10. Insertional amino acid sequence mutants are those in which one or more amino acid residues are introduced into a predetermined site in a protein although random insertion is also possible with suitable screening of the resulting product. Deletional mutants are characterized by the removal of one or more amino acids from the sequence. Substitutional amino acid mutants are those in which at least one residue in the sequence has been removed and a different residue inserted in its place. An example of substitutional amino acid mutants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Particular mutants are selected from the list consisting of:

| | |
|---|---|
| Bim: | D1A, M2A, R3A, P4A, E5A, I6A, W7A, I8A, A9E, Q10A, E11A, L12A, R13A, R14A, I15A, G16E, D17A, E18A, F19A, N20A, A21E, Y22A, Y23A, A24E, R25A and R26A; |
| Bad: | N1A, L2A, W3A, A4E, A5E, Q6A, R7A, Y8A, G9E, R10A, E11A, L12A, R13A, R14A, M15A, S16E, D17A, E18A, F19A, V20A, D21A, S22A, F23A, K24A, K25A and G26E; |

-continued

| | |
|---|---|
| Bid: | Q1A, E2A, D3A, I4A, I5A, R6A, N7A, I8A, A9E, R10A, H11A, L12A, A13E, Q14A, V15A, G16E, D17A, S18A, M19A, D20A, R21A, S22A, I23A, P24A, P25A and G26E; |
| mNoxaA: | R1A, A2E, E3A, L4A, P5A, P6A, E7A, F8A, A9E, A10E, Q11A, L12A, R13A, K14A, I15A, G16E, D17A, K18A, V19A, Y20A, C21A, T22A, W23A, S24A, A25E and D26A |
| Bak: | P1A, S2A, S3A, T4A, M5A, G6E, Q7A, V8A, G9E, R10A, Q11A, L12A, A13E, I14A, I15A, G16E, D17A, D18A, I19A, N20A, R21A, R22A, Y23A, D24A, S25A and E26A. |

By "detecting" as used in part c) above, is meant direct detection of binding on indirect via the function of the pro-survival or pro-apoptotic molecule.

In one embodiment, the amino acid residues within the BH3 domains are systematically mutated. In certain aspects of the present invention, the amino acid residues are substituted with an alanine, or in a case where an alanine or glycine is present in the wild-type sequence, an amino acid with difference properties is substituted. For example, glutamic acid, which is larger in size and charge when compared to an alanine or glycine.

Binding, or the lack thereof, between a mutated BH3 domain and a member of the pro-survival Bcl-2 family of proteins can be determined using screening assays. Examples of such screening assays include without being limited to, ELISAs, the yeast-two hybrid screening assay, or any other assays which is capable of identifying an interaction between two target proteins.

For example, in one screening assay, the mutated BH3 domain is fused to the gene-3 minor coat protein sequence of an M13 phage. Pro-survival proteins, such as Bcl-2, Bcl-$x_L$, Bcl-w, Mcl-1 or A1, are then incubated at varying concentrations with a fixed dilution of a phage displaying the mutated BH3 protein. An IC50 is then determined for the binding interaction between a given BH3 mutant and a member of the pro-survival Bcl-2 family of proteins.

BH3 mutants which do not bind or show a decreased ability to bind to one or more members of the Bcl-2 family of proteins identifies amino acid residues which are associated with the binding of a BH3-only protein to a Bcl-2 protein.

A binding assay may simply test binding of a test compound to the polypeptide, wherein binding is detected by a fluorophore, radioisotope, enzyme conjugate, or other detectable label. For example, the assay may comprise the steps of combining at least one BH3-mutant with at least one Bcl-2 protein, either in solution or affixed to a solid support, and detecting the binding of Bcl-2 to the BH3-mutant. Alternatively, the assay may detect or measure binding of the BH3-mutant in the presence of a labeled competitor. Additionally, the assay may be carried out using cell-free preparations, chemical libraries, or natural product mixtures, and the BH3-mutants may be free in solution or affixed to a solid support. Examples of such assays include radio-labeling assays such as those described in U.S. Pat. No. 5,914,236 and U.S. Pat. No. 6,372,724.

A mutant BH3-domain or a mutant BH3-domain fragments may be used to screen for compounds that modulate the activity of a Bcl-2 protein. Such compounds may include agonists, antagonists, or partial or inverse agonists. In one embodiment, an assay is performed under conditions permissive for BH3 binding to Bcl-2, wherein a BH3-domain is combined with at least one test compound, and the ability of the BH3 domain to induce apoptosis in the presence of a test compound is compared with the ability of the BH3-domain to induce apoptosis in the absence of the test compound. A change in the level of apoptosis in the presence of the test compound is indicative of a compound that modulates the activity of Bcl-2. Alternatively, a test compound is combined with an in vitro or cell-free system comprising BH3 under conditions suitable for BH3 to bind to Bcl-2, and the assay is performed. In either of these assays, a test compound which modulates the ability of BH3 to induce apoptosis may do so indirectly and need not come in direct contact with the test compound. At least one and up to a plurality of test compounds may be screened.

As used herein, a "BH3 domain protein" may include either the full length BH3 domain, or a portion thereof. A full-length BH3 domain may be either in the context of a whole BH3-only protein, or may be used in an isolated form. The BH3 proteins of the present invention may either be naturally occurring proteins, recombinantly generated or may be synthetic peptides.

A "fragment" is a unique portion of a BH3-domain or a polynucleotide encoding a BH3-domain which can be identical in sequence to, but shorter in length than, the parent sequence. A fragment may comprise up to the entire length of the defined sequence, minus one nucleotide/amino acid residue. For example, a fragment may comprise from about 5 to about 1000 contiguous nucleotides or amino acid residues. A fragment used as a probe, primer, antigen, therapeutic molecule, or for other purposes, may be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, or at least 500 contiguous nucleotides or amino acid residues in length. Fragments may be preferentially selected from certain regions of a molecule. Clearly these lengths are exemplary, and any length that is supported by the specification, including the Sequence Listing, tables, and figures, may be encompassed by the present embodiments The present invention is directed, in part, to the generation of agents which modulate the function of Bcl-2 proteins, thereby either functioning to increase apoptosis.

As used herein "antagonist" refers to a molecule which inhibits or attenuates the biological activity of a Bcl-2 protein. Antagonists may include proteins such as antibodies, anticalins, nucleic acids, carbohydrates, small molecules, or any other compound or composition which increases a susceptibility of a cell or cell population to apoptosis by directly interacting with a Bcl-2 protein or by acting on components of the biological pathway in which BH3-only proteins and/or Bcl-2 proteins participates.

Reference herein to an "agent" should be understood as a reference to any proteinaceous or nonproteinaceous molecule derived from natural, recombinant or synthetic sources. Useful sources include the screening of naturally produced libraries, chemical molecule libraries as well as combinatorial libraries, phage display libraries and in vitro translationbased libraries. Particularly useful sources are the modification of a promiscuous BH3 only domain to generate molecules which either antagonise or agonise the interaction between. In a particularly useful embodiment, the agent is a peptide or protein based on the BH3-only pro-apoptotic protein having at least one mutation in an amino acid residue listed in one or SEQ ID NOs:1 through 10.

In one embodiment, the agents of the present invention useful for the complete suppression of, or substantial decrease in, the levels or activity of the pro-survival functions of Bcl-2 or a pro-survival relative may be proteinaceous or chemical molecules. All such decreases, inhibitions, reductions and down-regulations of a Bcl-2 family protein pro-survival activity are encompassed by the terms "antagonist" or "antagonism" or "antagonizing". The result of these agents is to induce or render a cell or cell population susceptible to apoptosis.

In relation to agents which are proteinaceous molecules, such molecules include peptides, polypeptide and proteins. In addition, the terms mutant, part, derivative, homolog, analog or mimetic are meant to encompass various forms of an agent which completely suppresses or substantially decreases the pro-survival functions of Bcl-2 family protein.

The agents may be naturally occurring or artificially generated molecules. The agents may be BH-3 only proteins or BH3-domains or fragments thereof comprising one or more amino acid substitutions, deletions or additions. Agents may be generated by mutagenesis or other chemical methods or generated recombinantly or synthetically. Alanine scanning is a useful technique for identifying important amino acids (Wells, *Methods Enzymol* 202:2699-2705, 1991). In this technique, an amino acid residue is replaced by Alanine and its effect on the peptide's activity is determined. Each of the amino acid residues of the agent is analyzed in this manner to determine the important structural and/or charge and/or conformational and/or hydrophobic/hydrophilic regions. Agents are tested for their ability to bind to Bcl-2 and for other qualities such as longevity, binding affinity, dissociation rate, ability to cross membranes or ability to induce apoptosis.

Agents of the present invention may also encompass Bcl-2 binding portions of a full-length BH3-only protein. Portions are at least 1, at least 10, least 20 and at least 30 contiguous aminoacids, such as 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 amino acids which define a Bcl-2 binding fragment such as an amphipathic α-helix structure. It is proposed that this structure interacts with the hydrophobic grooves of the Bcl-2 proteins. Peptides of this type may be obtained through the application of standard recombinant nucleic acid techniques or synthesized using conventional liquid, or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of an amino acid sequence of the invention with proteinases such as endoLys-C, endoArg-C, endoGlu-C and staphylococcus V8-protease. The digested fragments can be purified by, for example, high performance liquid chromatographic (HPLC) techniques. Any such fragment, irrespective of its means of generation, is to be understood as being encompassed by the term "antagonist" as used herein.

Thus antagonists may comprise a derivative of a BH3-domain. Such a derivative includes parts, mutants, homologs, fragments, analogues as well as hybrid or fusion molecules and glycosylation variants of a BH3-domain or BH3-only protein. Derivatives also include molecules having a percent amino acid sequence identity over a window of comparison after optimal alignment. Preferably, the percentage similarity between a particular sequence and a reference sequence is at least about 60% or at least about 70% or at least about 80% or at least about 90% or at least about 95% or above such as at least about 96%, 97%, 98%, 99% or greater. Preferably, the percentage similarity between species, functional or structural homologs of the instant agents is at least about 60% or at least about 70% or at least about 80% or at least about 90% or at least about 95% or above such as at least about 96%, 97%, 98%, 99% or greater. Percentage similarities or identities between 60% and 100% are also contemplated such as 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

Analogs of residues in a protein antagonist such as a derivative of a BH3-only protein or BH3 domain contemplated herein include but are not limited to modification to side chains, incorporating unnatural amino acids and/or their derivatives during peptide, polypeptide or protein synthesis and the use of crosslinkers and other methods which impose conformational constraints on the proteinaceous molecule or their analogs. This term also does not exclude modifications of the polypeptide, for example, glycosylations, acetylations, phosphorylations and the like. Included within the definition are, for example, polypeptides containing one or more analogs of an amino acid (including, for example, unnatural amino acids such as those given in Table 2) or polypeptides with substituted linkages. Such polypeptides may need to be able to enter the cell.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids, contemplated herein is shown in Table 2. Such unnatural amino acids may be useful in conferring a tertiary structure analogous to a BH3 domain.

TABLE 2

CODES FOR NON-CONVENTIONAL AMINO ACIDS

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |

TABLE 2-continued

CODES FOR NON-CONVENTIONAL AMINO ACIDS

| Non-conventional amino acid | Code | Non-conventional amino acid | Code |
|---|---|---|---|
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

Reference to a mimetic of a BH3-domain includes a target binder (i.e. a BH3-only protein) at the structural and/or functional level and inhibits a pro-survival Bcl-2-protein. In accordance with one embodiment of the present invention, it is proposed to generate selected BH3-domain mimetics. A BH3-domain mimetic is designed based on structural differences between BH3 domains which have mutations which prevent binding to a Bcl-2 protein.

A peptide mimetic may be a peptide-containing molecule that mimics elements of protein secondary structure (Johnson et al., *Peptide Turn Mimetics in Biotechnology and Pharmacy*, Pezzuto et al., Eds., Chapman and Hall, New York, 1993). The underlying rationale behind the use of peptide mimetics is that the peptide backbone of proteins exists chiefly to orient amino acid side chains in such a way as to facilitate molecular interactions such as those of antibody and antigen, enzyme and substrate or scaffolding proteins. A peptide mimetic is designed to permit molecular interactions similar to the natural molecule. Peptide or non-peptide mimetics of a BH3-domain may be useful in the present invention as an agent which decreases the pro-survival function of Bcl-2, and thereby induces or renders a cell or cell population susceptible to apoptosis.

The designing of mimetics to a pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g. by substituting each residue in turn. As described hereinbefore, Alanine scans of peptides are commonly used to refine such peptide motifs. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic. Modelling can be used to generate inhibitors which interact with the linear sequence or a three-dimensional configuration.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

The goal of rational drug design in accordance with the present invention is to use computational methods to generate and/or select structural analogs of restrictive BH3-only proteins in order to fashion drugs which are, for example, more active or stable forms of the polypeptide and which have a restrictive binding spectrum. In one approach, one first determines the three-dimensional structure of a protein of interest by x-ray crystallography, by computer modelling or most typically, by a combination of approaches. Useful information regarding the structure of a polypeptide may also be gained by modelling based on the structure of homologous proteins. An example of rational drug design is the development of HIV protease inhibitors (Erickson et al., *Science* 249:527-533, 1990).

One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, the formation of complexes between a target or fragment and the agent being tested, or examine the degree to which the formation of a complex between a target or fragment and a known ligand is aided or interfered with by the agent being tested.

The screening procedure includes assaying (i) for the presence of a complex between the drug and the target, or (ii) an alteration in the expression levels of nucleic acid molecules encoding the target. One form of assay involves competitive binding assays. In such competitive binding assays, the target is typically labeled. Free target is separated from any putative complex and the amount of free (i.e. uncomplexed) label is a measure of the binding of the agent being tested to target molecule. One may also measure the amount of bound, rather than free, target. It is also possible to label the compound rather than the target and to measure the amount of compound binding to target in the presence and in the absence of the drug being tested.

Another technique for drug screening provides high throughput screening for compounds having suitable binding affinity to a target and is described in detail in Geysen (International Patent Publication No. WO 84/03564). Briefly stated, large numbers of different small peptide test compounds are synthesized on a solid substrate, such as plastic pins or some other surface. The peptide test compounds are reacted with a target and washed. Bound target molecule is then detected by methods well known in the art. This method may be adapted for screening for non-peptide, chemical entities. This aspect, therefore, extends to combinatorial approaches to screening for target antagonists or agonists.

Purified target can be coated directly onto plates for use in the aforementioned drug screening techniques. However, non-neutralizing antibodies to the target may also be used to immobilize the target on the solid phase. The target may alternatively be expressed as a fusion protein with a tag conveniently chosen to facilitate binding and identification.

In another embodiment, high throughput chemical screening (HTCS) for inhibitors of a Bcl-2 protein and Bcl-w can be carried out. Given the interaction of a BH3-only protein like Bim with a pro-survival Bcl-2 molecule precipitates apoptosis, libraries can be screened for small organic molecules that bind to the pro-survival proteins in such a way as to prevent BH3 binding. Multiple screening campaigns can be undertaken in order to identify compounds that target one or both anti-apoptotic molecules.

The proteins necessary for the high capacity assays may be produced in bacteria and initial studies using an optical biosensor (BiaCore) show that a biotinylated BH3 peptide binds a His6-tagged Bcl-2 protein with high affinity ($K_d$~11 nM) (Hinds et al, *EMBO Journal* 22:1497-1507, 2003). The high capacity binding assays necessary for HTCS have been developed using ALPHASCREEN™ (Amplified Luminescent Proximity Homogeneous Assay) technology (Glickman et al., *J Biomol Screen* 7:3-10, 2002). By revealing changes in fluorescence output as two partner proteins interact, it can monitor protein interactions with exquisite sensitivity. ALPHASCREEN™ is well suited for HTCS, as it is robust and can readily be carried out in small volumes as a homogenous assay with great dynamic range.

In one embodiment $His_6$ Bcl-2 is bound to nickel-coated acceptor beads and the biotinylated BH3 peptide is bound to the streptavidin-coated donor beads. The beads are then incubated with the test compounds in the wells of a 384-well microtitre plate (one test compound per well) and the assay results read using the Fusion alpha plate reader. The binding assay may be optimized with respect to the concentration of the protein partners and beads, incubation times and assay volumes so that the assay typically yields a signal to background ratio of >30:1. The assay has been validated as the $IC_{50}$ values obtained for a series of peptides were comparable with those obtained using an optical biosensor. Although the affinities of the peptides spanned over 3-orders of magnitude (8 nM-35 µM), the strong correlation observed between the two sets of results ($R^2$=0.9983) indicates that the assays measure the same interactions. The binding assays for $His_6$ Bcl-2 Δ/BH3 may also be optimized. Once the assay is optimised, it could be subjected to a rigorous quality control to assess plate-to-plate and day-to-day reproducibility. Each assay could then be used to screen a unique discovery library. To eliminate false positives, all inhibitory compounds that meet the target potency (IC50<25 µM) may be validated in secondary competition assays (AlphaScreen™, fluorescence polarisation and BiaCore optical biosensor). The optical biosensor facilitates to quantify the interactions between Bcl-2 family members, and ready comparison between the affinities of strong candidates to the physiological binding by BH3-only proteins can be made.

Compounds that pass these initial tests may be checked for identity and purity by, inter alia, liquid chromatography-mass spectrometry and then tested for their target specificity, i.e. affinity for Bcl-2, Bcl-$x_L$, Bcl-w, Mcl-1 or A1. Active compounds will also be tested in assays designed to predict intestinal absorption (Wohnsland et al., *J Med Chem* 44:923-930, 2001) and hepatotoxicity. In addition, in silico methods may be used to predict their bio-distribution properties, and to exclude pharmacophores that could present metabolic or toxicity problems (Drug Metabolism Databases and High-Throughput Testing During Drug Design and Development, Ed Erhardt, Blackwell Science, Malden, Mass., USA, 1999). The data on all the active compounds may be ranked by potency in binding assays, target selectivity, favourable predictive ADMET (Adsorption, Distribution, Metabolism, Excretion and Toxicity) properties (van de Waterbeemd and Gifford, *Nat Rev Drug Disc* 2:192-204, 2003) and chemical tractability. Then, all available close structural analogues of the top compounds may be obtained and tested for inhibitory activity in binding and killing assays to determine preliminary structure-activity relationships for each structural series.

In respect of assays on lead compounds for biological activity, when promising leads are found, their activity on cell viability in culture may be assessed. Up to 50 lead compounds, optimised according to the criteria described above, may be tested on a panel of cultured Tumorigenic and non-Tumorigenic cell lines, as well as primary mouse and human cell populations, e.g. lymphocytes. Cell viability may be monitored over 3-7 days of incubation with 1 nM-100 μM of the compounds. Greatest attention will, of course, be given to compounds that kill Tumor cells much more efficiently than their normal cell counterparts. Compounds that kill at <10 μM may be evaluated for the specificity of their targets and mode of action. Verifying their mode of action is important, because a test compound might well kill cells indirectly. For example, if a lead compound binds with high selectivity to Bcl-2, it should not kill cells lacking Bcl-2. Hence, the specificity of action may be confirmed by comparing the activity of the compound in wild-type cells with those lacking Bcl-2.

The most promising candidates may be subjected to a thorough analysis of their anti-Tumor efficacy in mouse models. In two models that have fully characterised previously, immuno-competent mice injected with B-cell lymphomas, derived from either myc transgenic mice (Adams et al., Nature 318:533-538, 1985) or myc/bcl-2 doubly transgenic animals (Strasser et al., Supra), succumb rapidly and reproducibly to a leukemia/lymphoma syndrome. Although both tumors respond to standard chemotherapy (cyclophosphamide), mice injected with myc/bcl-2 Tumor cells invariably relapse. These two transplantable Tumors will allow testing of any compounds, given alone or in combination with cyclophosphamide, in treating these malignancies which closely model human lymphomas.

In respect of structure-activity relationships (SAR) of the lead compounds and their optimisation, the leads selected from initial screens may require considerable modification to enhance their biochemical, biological and pharmacological properties (Bleicher et al., Nat Rev Drug Discov 2:369-378, 2003). To aid optimisation of these compounds, their mode of action may be verified in biochemical and structural studies. Furthermore, complexes formed between the agents and the pro-survival molecules may be analysed by NMR spectroscopy. Because NMR can detect ligands of low affinity and reveal where on the target protein they bind, it can greatly aid the optimisation of binding and accelerate the drug discovery process (Hajduk et al., J Med Chem 42:2315-2317, 1999; Pellecchia et al., Nat Rev Drug Discov 1:211-219, 2002). Using techniques such as chemical shift mapping, binding of test compounds to Bcl-2 proteins will be monitored and those mimicking a BH3 domain will be selected for optimisation.

In a related approach, molecular modelling of the lead agents may be performed to assess their binding in silico using an adapted DOCK program (Kuntz, Science 257:1078-1082, 1992). Lead compounds will be modelled onto the target Bcl-2 groove and scoring functions used to predict the most likely binding modes. This will guide the design of derivatives that provide additional interactions to enhance binding. The availability of NMR-derived experimental data also makes it possible to dock the ligand and the target flexibly in order to predict improved ligands (Lugovskoy et al., J Am Chem Soc 124:1234-1240, 2002).

This information and those from biological assays may be used to synthesise derivative compounds for further testing. For each class of lead compound, a strategy for synthesising derivatives. For example, a typical hit compound is composed of two or three linked ring systems, each of which may be substituted by a range of functional groups. By systematically replacing each of the functional groups, compounds with a wide range of chemical properties can be made and tested.

Agents identified in accordance with the present invention are useful in the treatment of cancer or hyperproliferative diseases or disorders.

Reference herein to "ameliorating" may mean a reduction in the severity of an existing condition. The term "ameliorate" is also taken to encompass "prophylactic measures" to prevent the onset of a condition. The term "ameliorate" does not necessarily imply that a subject is treated until total recovery. Similarly, "prophylasis" does not necessarily mean that the subject will not eventually contract a condition.

Subject as used herein refers to humans and non-human primates (e.g. gorilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), reptiles or amphibians (e.g. cane toad), fish (e.g. zebrafish) and any other organisms (e.g. *c. elegans*) who can benefit from the agents of the present invention. There is no limitation on the type of animal that could benefit from the presently described agents. The most preferred subject of the present invention is a human. A subject regardless of whether it is a human or non-human organism may be referred to as a patient, individual, animal, host or recipient.

Accordingly, another aspect of the present invention provides a method of preventing or reducing cancer or a disease associated with hyperproliferation in a subject said method comprising administering to said subject an effective amount of an antagonist of a Bcl-2 protein for a time and under conditions sufficient to prevent or decrease cancer or a hypoliferative disorder.

The identification of agents, capable of antagonizing Bcl-2 and inducing apoptosis provides pharmaceutical compositions for use in the therapeutic treatment of cancer.

The agents of the present invention can be combined with one or more pharmaceutically acceptable carriers and/or diluents to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., Remington's Pharmaceutical Sciences, 18$^{th}$ Edition, Mack Publishing Company, Easton, Pa., 1990 ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the modulatory agent of the invention and on its particular physio-chemical characteristics.

Administration of the agent, in the form of a pharmaceutical composition, may be performed by any convenient means known to one skilled in the art. Routes of administration include, but are not limited to, respiratorally, intratracheally, nasopharyngeally, intravenously, intraperitoneally, subcutaneously, intracranially, intradermally, intramuscularly, intraoccularly, intrathecally, intracerebrally, intranasally, infusion, orally, rectally, patch and implant.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier, see, e.g, International Patent Publication Number WO 96/11698.

Agents of the present invention, when administered orally, may be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g. Fix, *Pharm Res* 13:1760-1764, 1996; Samanen et al., *J Pharm Pharmacol* 48:119-135, 1996; U.S. Pat. No. 5,391,377, describing lipid compositions for oral delivery of therapeutic agents (liposomal delivery is discussed in further detail, infra).

The pharmaceutical forms suitable for injectable use include sterile aqueous solutions (where water-soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the agents in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For parenteral administration, the agent may dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the agents are being administered intrathecally, they may also be dissolved in cerebrospinal fluid.

For transmucosal or transdermal administration, penetrants appropriate to the barrier to be permeated can be used for delivering the agent. Such penetrants are generally known in the art e.g. for transmucosal administration, bile salts and fusidic acid derivatives. In addition, detergents can be used to facilitate permeation. Transmucosal administration can be through nasal sprays or using suppositories e.g. Sayani and Chien, *Crit Rev Ther Drug Carrier Syst* 13:85-184, 1996. For topical, transdermal administration, the agents are formulated into ointments, creams, salves, powders and gels. Transdermal delivery systems can also include patches.

For inhalation, the agents of the invention can be delivered using any system known in the art, including dry powder aerosols, liquids delivery systems, air jet nebulizers, propellant systems, and the like, see, e.g., Patton, *Nat Biotech* 16:141-143, 1998; product and inhalation delivery systems for polypeptide macromolecules by, e.g., Dura Pharmaceuticals (San Diego, Calif.), Aradigm Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, for example, air jet nebulizers.

The agents of the invention can also be administered in sustained delivery or sustained release mechanisms, which can deliver the formulation internally. For example, biodegradable microspheres or capsules or other biodegradable polymer configurations capable of sustained delivery of a peptide can be included in the formulations of the invention (e.g. Putney and Burke, *Nat Biotech* 16:153-157, 1998).

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's.

In one aspect, the pharmaceutical formulations comprising agents of the present invention are incorporated in lipid monolayers or bilayers such as liposomes, see, e.g., U.S. Pat.

Nos. 6,110,490; 6,096,716; 5,283,185 and 5,279,833. The invention also provides formulations in which water-soluble modulatory agents of the invention have been attached to the surface of the monolayer or bilayer. For example, peptides can be attached to hydrazide-PEG-(distearoylphosphatidyl) ethanolamine-containing liposomes (e.g. Zalipsky et al., *Bioconjug Chem* 6:705-708, 1995). Liposomes or any form of lipid membrane, such as planar lipid membranes or the cell membrane of an intact cell e.g. a red blood cell, can be used. Liposomal formulations can be by any means, including administration intravenously, transdermally (Vutla et al., *J Pharm Sci* 85:5-8, 1996), transmucosally, or orally. The invention also provides pharmaceutical preparations in which the nucleic acid, peptides and/or polypeptides of the invention are incorporated within micelles and/or liposomes (Suntres and Shek, *J Pharm Pharmacol* 46:23-28, 1994; Woodle et al., *Pharm Res* 9:260-265, 1992). Liposomes and liposomal formulations can be prepared according to standard methods and are also well known in the art see, e.g., Remington's; Akimaru et al., *Cytokines Mol Ther* 1:197-210, 1995; Alving et al., *Immunol Rev* 145:5-31, 1995; Szoka and Papahadjopoulos, *Ann Rev Biophys Bioeng* 9:467-508, 1980, U.S. Pat. Nos. 4,235,871, 4,501,728 and 4,837,028.

The pharmaceutical compositions of the invention can be administered in a variety of unit dosage forms depending upon the method of administration. Dosages for typical pharmaceutical compositions are well known to those of skill in the art. Such dosages are typically advisorial in nature and are adjusted depending on the particular therapeutic context, patient tolerance, etc. The amount of agent adequate to accomplish this is defined as the "effective amount". The dosage schedule and effective amounts for this use, i.e., the "dosing regimen" will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., Remington's; Egleton and Davis, *Peptides* 18:1431-1439, 1997; Langer, *Science* 249:1527-1533, 1990.

In accordance with these methods, the agents and/or pharmaceutical compositions defined in accordance with the present invention may be co-administered with one or more other agents. Reference herein to "co-administered" means simultaneous administration in the same formulation or in two different formulations via the same or different routes or sequential administration by the same or different routes. Reference herein to "sequential" administration is meant a time difference of from seconds, minutes, hours or days between the administration of the two types of agents and/or pharmaceutical compositions. Co-administration of the agents and/or pharmaceutical compositions may occur in any order.

Alternatively, targeting therapies may be used to deliver the active agent more specifically to certain types of cell, by the use of targeting systems such as antibodies or cell specific ligands or specific nucleic acid molecules. Targeting may be desirable for a variety of reasons, e.g. if the agent is unacceptably toxic or if it would otherwise require too high a dosage or if it would not otherwise be able to enter the target cells.

Instead of administering the agents directly, they could be produced in the target cell, e.g. in a viral vector such as described above or in a cell based delivery system such as described in U.S. Pat. No. 5,550,050 and International Patent Publication Numbers WO 92/19195, WO 94/25503, WO 95/01203, WO 95/05452, WO 96/02286, WO 96/02646, WO 96/40871, WO 96/40959 and WO 97/12635. The vector could be targeted to the target cells. The cell based delivery system is designed to be implanted in a patient's body at the desired target site and contains a coding sequence for the target agent. Alternatively, the agent could be administered in a precursor form for conversion to the active form by an activating agent produced in, or targeted to, the cells to be treated. See, for example, European Patent Application Number 0 425 731A and International Patent Publication Number WO 90/07936.

In yet another aspect, the present invention provides kits comprising the compositions e.g. agents of the present invention. The kits can also contain instructional material teaching the methodologies and uses of the invention, as described herein.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The present invention is further described by the following non-limiting examples.

EXAMPLE 1

BH3 Domain Mutants

Recombinant Proteins and Synthetic Peptides

All recombinant proteins were expressed in *E. coli* using standard techniques. Recombinant human Bcl-$x_L$ with a 25 amino acid truncation of its C-terminus (Bcl-$x_L$ ΔC25) and mouse Mcl-1 with truncations of 151 amino acid residues at its N-terminus and 23 residues at its C-terminus (Mcl-1ΔN151ΔC23) were expressed as GST fusion proteins and cleaved off Glutathione-Sepharose columns with PreScission protease and purified as described previously (Day et al. *Cell Death and Differentiation* 6:1125-1132, 1999; Hinds et al. 2003 supra). The synthetic peptides were synthesized by Mimotopes (Victoria, Australia), purified by reverse-phase HPLC with >90% purity. All peptides correspond to human BH3 domain sequences unless otherwise stated. Their identities were confirmed by electrospray mass spectrometry. Peptides were weighed, dissolved in water as stock solutions of 1-2 mM and their concentration confirmed by measuring their absorbance at 280 nm prior to testing.

Phage Display Constructs

Twenty-six amino acids long peptides encompassing the BH3 domains of Bim (DMRPEIWIAQELRRIGDEFNAY-YARR) (SEQ ID NO:1) or Bad (NLWAAQRYGRELRRMS-DEFVDSFKKG) (SEQ ID NO:4), or mNoxaA (SEQ ID 9) or Bid (SEQ ID 7 or Bak (SEQ ID 11) were fused via a linker sequence (GGGT) to the amino terminus of the M13 phage gene 3 (residues 249-406) sequence using complementary oligonucleotides which also created NcoI and KpnI restriction enzyme sites at the 5' and 3' ends respectively for cloning into the phagemid vector described previously Fairlie et al. *Protein Expression and Purification* 26:171-178, 2002. The residues in the above peptide sequences are hereafter referred to by their sequence position within the 26-mer. In order to create a FLAG-tagged form of the sequence, an oligonucleotide encoding the FLAG epitope was employed to loop-in the required sequence at the N-terminus of the peptide sequences, already fused to gene 3 as described above, using the Kunkel mutagenesis method (Kunkel et al. *Methods Enzymol* 204:125-139, 1991). For the alanine scanning constructs and other point mutations of the BimBH3 or other BH3 sequence, oligonucleotides with the desired codon mismatch were employed in Kunkel mutagenesis reactions on the FLAG-BimBH3 or FLAG-BadBH3 template. The mutagenesis reactions were chemically transformed into the SS320 *E. coli* strain and after overnight growth in the presence of M13 K07 helper phage, phage particles were isolated from cell supernatants by saline/polyethylene glycol precipitation as described previously (Sidhu et al. *Methods Enzymol* 328:333-363, 2000).

EXAMPLE 2

BH3/Bcl-2 Binding Interactions

Phage ELISA

All ELISA's were performed as described previously (Fairlie et al. *J Biol Chem* 279:2125-2134, 2004). In each case, either the pro-survival Bcl-2-like family protein (5 µg/mL) or M2 anti-FLAG antibody (0.5 µg/mL) were coated onto Maxisorp 96-well plates overnight at 4° C. After blocking with 6% (w/v) skim milk in PBS, phage were added at appropriate dilutions in PBS/0.1% (v/v) Tween-20/1% (w/v) skim milk and incubated for 1.5 hours at room temperature with shaking. Following washing with PBS/Tween, bound phage were detected using a horseradish peroxidase-conjugated anti-M13 antibody. For the competition assays, various concentrations of Bcl-2-like proteins in solution were used to displace a fixed sub-saturating dilution of phage-displayed BimBH3 or other BH3 peptide from binding to immobilized Bcl-2-like proteins by co-incubation for 1.5 hours at room temperature. The $IC_{50}$ values of the alanine scanning mutants for the pro-survival proteins were divided by that of the wild-type BimBH3 or BadBH3 in order to determine either the decrease or increase in binding affinity over the native sequences.

Surface Plasmon Resonance

The relative affinities of the wild-type and mutant BimBH3 peptides for pro-survival Bcl-2 proteins were determined at room temperature using surface plasmon resonance on a Biacore 0.3000 biosensor with HBS (10 mM HEPES pH 7.2, 150 mM NaCl, 3.4 mM EDTA, 0.005% Tween 20) as the running buffer. A 26-mer BimBH3 and a control non-binding BimBH3 mutant were immobilized using amine-coupling chemistry (Wilson-Annan et al, Supra). The relative affinities of BH3 peptides for pro-survival Bcl-2-like proteins were assessed by comparing their abilities to compete with immobilized BimBH3 peptide for binding to Bcl-2-like proteins (Wilson-Annan et al. *Journal of Cell Biology* 162:877-888, 2003; Chen et al. *Mol Cell* 17:393-403, 2005) by incubation of a fixed sub-saturating concentration (approximately 10 nM) of a pro-survival Bcl-2 protein with varying amounts of competitor BH3 peptide in HBS for >2 h on ice. The mixtures were then injected over the CM5 sensor chip containing a channel onto which wild-type BimBH3 was immobilized and a control channel with a non-binding BimBH3 mutant immobilized. The baseline response (control channel) was subtracted to obtain the absolute binding response. Data was then analysed as previously described (Chen et al. 2005 supra).

Retrovirus Assays

Parental pMIG plasmid DNA or pMIG containing an insert encoding Bim or Bim mutants were transiently transfected, using LIPOFECTAMINE™ (Invitrogen), into Phoenix Ecotropic packaging cells (On the World-Wide-Web at stanford-.edu/group/nolan/retroviral_systems/phx.htmD (Kinesella and Nolan, 1996). Filtered virus-containing supernatants were used to infect 3T9 Mouse Embryonic Fibroblasts (MEFs) by spin inoculation (2,500 rpm radial centrifugation at 32° C. for 45 min in the presence of 4 µg/mL polybrene; Sigma). Infection efficiency of over 90% was obtained routinely. SV40 large T-antigen immortalized wild-type and $Bax^{-/-}Bak^{-/-}$ MEFS were obtained from Professor Stanley Korsmeyer and maintained in full DME. Cell viability (for short-term survival assays) was determined by flow cytometric analyses of infected cells ($GFP^{+ve}$; FL-1) that excluded 5 µg/mL propidium iodide (Sigma) (FL-3) analysed by using FACSCAN™; fluorescence activated cell sorting (Becton Dickinson).

EXAMPLE 3

Expression of the BH3 Domain of Bim and Bad on Phage and its Binding to Pro-Survival Bcl-2 Family Proteins Prior to performing any structure-function analysis of the BimBH3 and other BH3 domains, it was first necessary to determine whether the sequences could be displayed on phage and, that it functioned in a manner similar to that observed with, for example, BimBH3 or BadBH3 synthetic peptides binding to pro-survival Bcl-2 proteins in other biochemical assays. In an initial assay, the BimBH3 and other BH3 phage were tested for their ability to bind directly to immobilised $Bcl-x_L$ and Mcl-1. Relatively strong, titratable binding was observed for both BH3 domains to $Bcl-x_L$ whilst only Bim BH3 bound to Mcl-1. This is in accordance with previous data that has shown that Bim can bind all pro-survival proteins with high affinity whilst Bad is specific for $Bcl-x_L$, Bcl-2 and Bcl-w (Chen et al. 2005 supra). The specificity of the interactions were further assessed using a competition assay in which phage binding to the immobilised protein was competed with the corresponding recombinant protein in solution. The $IC_{50}$ values obtained are as presented in Table 3 and were very similar to those determined with BimBH3 and BadBH3 synthetic peptides as measured by surface plasmon resonance on a BIAcore instrument (Chen et al. 2005 supra) and using isothermal calorimetry (unpublished data).

TABLE 3

Binding affinities of the phage-displayed BH3 domains of BH3-only proteins for pro-survival Bcl-2-like proteins.

| BH3-only protein BH3 domain | pro-survival Bcl-2-like protein | IC50 value (nM) |
|---|---|---|
| BimBH3 | Bcl-xL | 3 |
| BimBH3 | Mcl-1 | 10 |
| BadBH3 | Bcl-xL | 1 |

Alanine Scanning Mutagenesis

In order to gain insight into the importance of particular residues within the BimBH3 or BadBH3 domain sequence for binding the Bcl-2-like pro-survival proteins, a set of mutant constructs were generated in which each residue was individually mutated to alanine, or in positions where alanine or glycine was the wild-type residue, to glutamic acids. Each mutant was monovalently expressed on M13 phage as a N-terminal fusion to g3 on M13 phage and tested for its ability to bind to immobilised pro-survival proteins, as well as to an anti-FLAG antibody. All of the constructs were generated with a FLAG epitope at the amino terminus as binding to the anti-FLAG antibody provided a means by which differences in expression levels between each peptide could be assessed. An initial titration assay was performed in order to determine a sub-saturating dilution of each mutant phage to use in the competition ELISA. In order to determine the binding affinities of the mutant peptides for the pro-survival proteins, the phage mutants were then tested in a competition ELISA using the sub-saturating dilution of phage determined in the titration assay. The affinities of phage display BH3 mutants for binding to one or more of Bcl-$X_L$, Bcl-w, Bcl-2 and/or Mcl-1 are shown in Tables 4a through 4e.

TABLE 4a

Affinities of phage display Bim BH3 mutants for binding to Bcl-$X_L$, Bcl-w, Bcl-2 and Mcl-1

| Bim | Bcl-$x_L$-<br>IC$_{50}$ (nM)<br>[Fold/wt] | Bcl-w-<br>IC$_{50}$ (nM)<br>[Fold/wt] | Bcl-2-<br>IC$_{50}$ (nM)<br>[Fold/wt] | Mcl-1-<br>IC$_{50}$ (nM)<br>[Fold/wt] |
|---|---|---|---|---|
| D1A | 3 (1) | 38 (2) | 6 (1) | 10 (1) |
| M2A | 4 (2) | 38 (2) | 6 (1) | 13 (1) |
| R3A | 3 (1) | 33 (2) | 6 (1) | 9 (1) |
| P4A | 3 (1) | 25 (1) | 5 (1) | 12 (1) |
| E5A | 3 (1) | 29 (1) | 5 (1) | 10 (1) |
| I6A | 8 (3) | 42 (2) | 7 (1) | 11 (1) |
| W7A | 3 (1) | 32 (2) | 7 (1) | 10 (1) |
| I8A | 7 (2) | 74 (4) | 17 (3) | 9 (1) |
| A9E | NB (NB) | NB (NB) | NB (NB) | 32 (3) |
| Q10A | 4 (1) | 37 (2) | 4 (1) | 10 (1) |
| E11A | 4 (1) | 23 (1) | 3 (1) | 10 (1) |
| L12A | 124 (43) | 486 (24) | NB (NB) | 10 (1) |
| R13A | 4 (1) | 55 (3) | 6 (1) | 13 (1) |
| R14A | 5 (2) | 36 (2) | 14 (3) | 10 (1) |
| I15A | 2 (1) | 18 (1) | 7 (1) | 10 (1) |
| G16E | NB (NB) | NB (NB) | NB (NB) | 27 (3) |
| D17A | NB (NB) | NB (NB) | NB (NB) | 256 (28) |
| E18A | 8 (3) | 65 (3) | 8 (1) | 80 (9) |
| F19A | 69 (24) | 364 (18) | 11 (2) | 16 (2) |
| N20A | 5 (2) | 58 (3) | 6 (1) | 7 (1) |
| A21E | 3 (1) | 24 (1) | 6 (1) | 16 (2) |
| Y22A | 4 (1) | 43 (2) | 8 (1) | 12 (1) |
| Y23A | 4 (1) | 52 (3) | 7 (1) | 12 (1) |
| A24E | 2 (1) | 30 (1) | 7 (1) | 8 (1) |
| R25A | 2 (1) | 14 (1) | 6 (1) | 8 (1) |
| R26A | 4 (1) | 21 (1) | 6 (1) | 8 (1) |
| wtBim | 3 (1) | 20 (1) | 5 (1) | 9 (1) |

NB = no binding
Fold/wt = folds per wild type

TABLE 4b

Affinities of phage display Bad BH3 mutants for binding to Bcl-$X_L$, Bcl-w and Bcl-2

| Bad | Bcl-$x_L$-<br>IC$_{50}$ (nM)<br>[Fold/wt] | Bcl-w-<br>IC$_{50}$ (nM)<br>[Fold/wt] | Bcl-2-<br>IC$_{50}$ (nM)<br>[Fold/wt] |
|---|---|---|---|
| N1A | 2 (1) | 47 (1) | 10 (1) |
| L2A | 4 (2) | 35 (1) | 7 (1) |
| W3A | 3 (1) | 33 (1) | 12 (1) |
| A4E | 4 (2) | 46 (1) | 10 (1) |
| A5E | 12 (5) | 152 (4) | 26 (2) |
| Q6A | 3 (2) | 47 (1) | 18 (1) |
| R7A | 4 (2) | 32 (1) | 14 (1) |
| Y8A | 7 (3) | 77 (2) | 19 (1) |
| G9E | NB (NB) | NB (NB) | NB (NB) |
| R10A | 3 (1) | 41 (1) | 14 (1) |
| E11A | No expression<br>(No expression) | No expression<br>(No expression) | No expression<br>(No expression) |
| L12A | NB (NB) | NB (NB) | NB (NB) |
| R13A | 3 (1) | 52 (1) | 19 (1) |
| R14A | 4 (2) | 86 (2) | 57 (5) |
| M15A | 6 (3) | 43 (1) | 43 (3) |
| S16E | NB (NB) | NB (NB) | NB (NB) |
| D17A | 16 (7) | 128 (3) | NB (NB) |
| E18A | 4 (2) | 55 (1) | 29 (2) |
| F19A | 27 (12) | NB (NB) | NB (NB) |
| V20A | 3 (1) | 38 (1) | 13 (1) |
| D21A | 2 (1) | 28 (1) | 17 (1) |
| S22A | 4 (2) | 77 (2) | 19 (1) |
| F23A | 4 (2) | 83 (2) | NB (NB) |
| K24A | 4 (1) | 54 (1) | 14 (1) |
| K25A | 4 (2) | 46 (1) | 13 (1) |
| G26E | 3 (1) | 37 (1) | 15 (1) |
| wtBad | 2 (1) | 37 (1) | 13 (1) |

TABLE 4c

Affinities of phage display Bid BH3 mutants for binding to Bcl-$X_L$, Bcl-w and Mcl-1

| Bid | Bcl-$x_L$-<br>IC$_{50}$ (nM)<br>[Fold/wt] | Bcl-w-<br>IC$_{50}$ (nM)<br>[Fold/wt] | Mcl-1-<br>IC$_{50}$ (nM)<br>[Fold/wt] |
|---|---|---|---|
| Q1A | 24 (2) | 29 (1) | 79 (1) |
| E2A | 12 (1) | 34 (2) | 140 (1) |
| D3A | 15 (1) | 34 (1) | 96 (1) |
| I4A | 31 (3) | 23 (1) | 134 (1) |
| I5A | 21 (2) | 34 (2) | 144 (1) |
| R6A | 31 (3) | 42 (2) | 88 (1) |
| N7A | 10 (1) | 25 (1) | 54 (1) |
| I8A | NB (NB) | 182 (8) | NB (NB) |
| A9E | NB (NB) | NB (NB) | NB (NB) |
| R10A | 26 (2) | 46 (2) | 130 (1) |
| H11A | 9 (1) | 17 (1) | 89 (1) |
| L12A | NB (NB) | 553 (25) | NB (NB) |
| A13E | NB (NB) | 253 (11) | NB (NB) |
| Q14A | 13 (1) | 25 (1) | 124 (1) |
| V15A | NB (NB) | 59 (3) | 245 (2) |
| G16E | NB (NB) | NB (NB) | NB (NB) |
| D17A | NB (NB) | NB (NB) | NB (NB) |
| S18A | 16 (1) | 31 (1) | 104 (1) |
| M19A | NB (NB) | NB (NB) | NB (NB) |
| D20A | 13 (1) | 24 (1) | 84 (1) |
| R21A | 32 (3) | 52 (2) | 132 (1) |
| S22A | 13 (1) | 27 (1) | 128 (1) |
| I23A | 15 (1) | 18 (1) | 142 (1) |
| P24A | 14 (1) | 25 (1) | 90 (1) |
| P25A | 16 (1) | 26 (1) | 87 (1) |
| G26E | 17 (2) | 25 (1) | 94 (1) |
| wtBid | 11 (1) | 23 (1) | 99 (1) |

TABLE 4d

Affinities of phage display mNoxa BH3 mutants for binding to Mcl-1

| mNoxaA | Mcl-1 - IC$_{50}$ (nM)<br>[Fold/wt] |
|---|---|
| R1A | 20 (1) |
| A2E | 22 (1) |
| E3A | 30 (1) |
| L4A | 24 (1) |
| P5A | 20 (1) |
| P6A | 8 (<1) |
| E7A | 43 (1) |
| F8A | 24 (1) |
| A9E | 76 (2) |

TABLE 4d-continued

Affinities of phage display mNoxa
BH3 mutants for binding to Mcl-1

| mNoxaA | Mcl-1 - IC$_{50}$ (nM) [Fold/wt] |
|---|---|
| A10E | 43 (1) |
| Q11A | 22 (1) |
| L12A | 67 (2) |
| R13A | 57 (1) |
| K14A | 37 (1) |
| I15A | NB (NB) |
| G16E | NB (NB) |
| D17A | NB (NB) |
| K18A | 11 (<1) |
| V19A | NB (NB) |
| Y20A | 32 (1) |
| C21A | 19 (1) |
| T22A | 14 (<1) |
| W23A | 69 (2) |
| S24A | 13 (<1) |
| A25E | 33 (1) |
| D26A | 62 (2) |
| wt | 39 (1) |

TABLE 4e

Affinities of phage display Bak BH3 mutants
for binding to Bcl-X$_L$ and Mcl-1

| Bak | Bcl-x$_L$ - IC$_{50}$ (nM) [Fold/wt] | Mcl-1 IC$_{50}$ (nM) [Fold/wt] |
|---|---|---|
| P1A | 31 (1) | 18 (1) |
| S2A | 28 (1) | 16 (1) |
| S3A | 25 (1) | 17 (1) |
| T4A | 28 (1) | 14 (1) |
| M5A | 15 (<1) | 18 (1) |
| G6E | 14 (<1) | 11 (1) |
| Q7A | 48 (1) | 20 (1) |
| V8A | NB (NB) | 79 (4) |
| G9E | NB (NB) | 438 (21) |
| R10A | 163 (3) | 29 (1) |
| Q11A | 238 (5) | 16 (1) |
| L12A | NB (NB) | 414 (20) |
| A13E | NB (NB) | 356 (17) |
| I14A | 66 (1) | 14 (1) |
| I15A | NB (NB) | 517 (25) |
| G16E | NB (NB) | NB (NB) |
| D17A | NB (NB) | NB (NB) |
| D18A | 33 (1) | 14 (1) |
| I19A | NB (NB) | 185 (9) |
| N20A | 111 (2) | 23 (1) |
| R21A | 87 (2) | 17 (1) |
| R22A | 37 (1) | 16 (1) |
| Y23A | 52 (1) | 117 (6) |
| D24A | 30 (1) | 9 (<1) |
| S25A | 31 (1) | 18 (1) |
| E26A | 29 (1) | 10 (<1) |
| wt | 49 (1) | 21 (1) |

BimBH3 Versus Bcl-x$_L$, Bcl-w and Bcl-2:

Refer to Table 4a. Three mutants, A9E, G16E, and D17A, did not appear to bind Bcl-x$_L$ in the initial titration even though binding to the anti-FLAG antibody was comparable to all the other mutants, indicating the effect observed was not a consequence of aberrant expression. For all but five of the mutants tested, the change in IC$_{50}$ values over BimBH3 binding only varied by a factor of less than four. As the binding of A9E, G16E, and D17A was weak, accurate quantitative affinity data could not be obtained for these mutants, however, binding of the L12A and F19A mutants was approximately 50- and 20-fold weaker (IC$_{50}$=130 nM and 60 nM) than wild-type BimBH3 respectively. It is known from the available structures of the complexes between various BH3-only proteins and pro-survival Bcl-2-like proteins, that four conserved hydrophobic residues within the BH3 domain sit in hydrophobic pockets found on the binding surfaces of all pro-survival proteins. It was therefore expected that these residues would make a significant contribution to the binding energy between the two families of proteins as seen with the L12A and F19A mutants above. Based on the results from the competition assay, it was therefore interesting to note that mutating the other two hydrophobic residues (other than L12 and F19), I8 and I15, to an alanine did not appear to have any significant effects on their binding to Bcl-x$_L$.

BimBH3 Versus Mcl-1

Refer to Table 4a. The majority of the BimBH3 alanine mutants tested against Mcl-1 did not appear to have a significant effect on binding as compared to their ability to bind to Bcl-x$_L$. Only two mutations, G16E (38-fold) and D17A (15-fold), had significant effects on binding to Mcl-1, though these effects were not as great as those observed for the same mutants binding to Bcl-x$_L$. Furthermore, in contrast to their interaction with Bcl-x$_L$, neither the L12A mutation nor F19A mutation had any detectable effects on binding. Once again, expression of the various mutants on the surface of the phage was confirmed by testing for binding against the FLAG antibody.

Taken together the results in Table 4a indicate that a Bim double mutant L12A/F19A should be selective for Mcl-1, unlike any naturally occurring BH3 only protein. This is shown in Example 5.

BadBH3 Versus Bcl-x Bcl-w and Bcl-2:

Refer to Table 4b. Similarly, the data presented suggest that a Bad BH3 domain with the mutant F19A will be selective for Bcl-xL, and with D17A or F23A is selective for Bcl-xL and Bcl-w BidBH3 Versus Bcl-xL, Bcl-w and Mcl-1:

Refer to Table 4c. Similarly the data presented suggest that Bid BH3 domain with the mutant I8A or A13E is selective for Bcl-w.

Bak BH3 Versus Bcl-xL and Mcl-1

Refer to Table 4e. A Bak BH3 with the mutation V8A or I19A will be selective for Mcl-1. Similarly a double mutant R10A/Q11A will be selective for Mcl-1.

As reflected in the data presented in Tables 4a through 4e, it is clear that the residues which make significant contributions to maintaining (or forming) the complexes are different between different BH3-only protein and pro-survival protein pairings. For example, the interaction between BimBH3 and Bcl-x$_L$ involves a number of residues including L12, F19 and particularly D17 whilst the BadBH3/Bcl-x$_L$ interaction is more dependent on the L12 contact.

EXAMPLE 4

Detailed Structure-Function Analysis of L12, D17 and F19

Once the key residues in a BH3 domain-pro-survival interaction have been identified through studies such as the alanine scanning mutagenesis described above, systematic replacement of these residues can then be performed to determine the physicochemical properties of the amino acids that are be tolerated at each of these positions. For example, in the case of L12 in BimBH3 which is important for binding to Bcl-x$_L$, the impact of replacing it with other larger hydrophobic residues such as isoleucine, tyrosine and phenylalanine or smaller ones such as valine, can be assessed. These binding affinities are then compared to the wild-type sequences as previously described. The data derived from such experiments can be utilised in small molecule peptidomimetic drug design. In the above example, if very weak binding was observed following replacement with tyrosine, phenylalanine and tryptophan, then small molecules designed to mimic the leucine interaction might avoid the use of cyclic groups as found in the above amino acid side chains. Alternatively, if the above residues are tolerated without significant decreases in affinity, then cyclic compounds of similar size could be incorporated.

In the case of BimBH3 binding to Bcl-$x_L$, a progressive decrease in binding affinity from 5- to 22-fold was observed as the size of the side-chain was increased from phenylalanine to tryptophan (Table 5). Similarly, decreases in side-chain length from valine to alanine resulted in approximately 50- to 80-fold decreases in affinity. Table 5 has substitutions at Bim BH3 positions 12, 17 and 19 that do not cause a reduction in affinity below 100 nM for four pro-survival molecules.

Bcl-2-like proteins. Both the I8A and I15A mutants retained wild-type binding affinities for all pro-survival proteins which is in good agreement with the results obtained from the phage ELISAs. The L12A mutant conferred a 30- to 70-fold decrease in binding affinities to Bcl-2, Bcl-w and Bcl-$x_L$, whilst binding to the remaining two pro-survival proteins, Mcl-1 and A1 was only slightly affected with a 2- and 7-fold decrease in binding affinity observed respectively. These results are in good agreement once again with the phage ELISA results as described previously. Binding of the F19A mutant peptide to the various pro-survival Bcl-2-like proteins appeared to be only slightly affected with the most significant effect being on its binding to Bcl-w where an 8-fold decrease in binding affinity was observed. There was less than a 3-fold decrease in binding affinity to the remaining pro-survival proteins.

TABLE 5

Bim BH3 mutants at L12, D17 and F19

Generic BH3 domain

| 8 | 9 | | 10 | | 11 | | 12 | | 13 | | 14 | | 15 | | 16 | | 17 | 18 19 |
|---|---|---|---|---|---|---|---|---|---|---|---|---|---|---|---|---|---|---|
| f1 | A/G | | x | | x | | f2 | | x | | x | | f3 | | A/G | | D | x f4 |
| | A | G | S | T | V | L | I | M | F | Y | W | D | E | N | Q | H | K | R | |
| L12 | | | + | | + | + | + | + | + | + | + | | | | | | | | Bcl-xL |
| D17 | nt | nt | nt | nt | nt | nt | nt | nt | nt | nt | nt | + | | + | nt | nt | nt | | <35-Fold; ~90 nM |
| F19 | + | | + | + | + | + | + | + | + | + | + | | | | + | | | | |
| L12 | | | + | | | + | + | + | + | + | + | | | | | | | | Bcl-w |
| D17 | nt | nt | nt | nt | nt | nt | nt | nt | nt | nt | nt | + | | | nt | nt | nt | | <5-Fold; 100 nM |
| F19 | | | | + | + | + | + | + | + | + | + | | | | + | | | | |
| L12 | | | | | | + | + | + | + | + | + | | | | | | | | Bcl-2 |
| D17 | nt | nt | nt | nt | nt | nt | nt | nt | nt | nt | nt | + | + | + | nt | nt | nt | | <20-Fold; 100 nM |
| F19 | + | + | + | + | + | + | + | + | + | + | + | | + | + | + | + | | + | |
| L12 | + | + | + | + | + | + | + | + | + | | + | | | | + | + | | | Mcl-1 |
| D17 | nt | nt | nt | nt | nt | nt | nt | nt | nt | nt | nt | + | + | + | nt | nt | nt | + | <13-Fold; ~100 nM |
| F19 | + | + | + | + | + | + | + | + | + | + | + | + | + | + | + | + | + | + | | f1/f3 = I Y F L M V W T
x ≠ P
nt: not tested

Together these results, along with structural analysis, provide a suitable framework for the design of small molecule compounds that mimic the action of Bim in binding to Bcl-$x_L$, Bcl-2, Bcl-w or Mcl-1. The data in Table 5 teach one how to make pro-survival specific BH3 sequences. Thus, a Bim BH3 containing a mutant at any one of L12A, L12Q, L12H, D17R, F19D, F19K is specific for Mcl-1, as may be selected combinations of the above.

EXAMPLE 5

BIAcore Studies

To further validate the phage display screening results, a number of peptides corresponding to sequences of interest were synthesized and tested in competition assays using surface plasmon resonance performed on a BIAcore instrument. In these experiments, the affinities of the peptides for all members of the pro-survival family (i.e. Bcl-2, Bcl-$x_L$, Bcl-w, Mcl-1 and A1) were determined and the results of these assays are as shown in Table 6. Four synthetic peptides in which each of the four conserved hydrophobic residues (I8, L12, I15, and F19) were individually mutated to an alanine were tested for their abilities to bind the various pro-survival

TABLE 6

Differences in binding affinities of BimBH3 mutant synthetic peptides over wild-type BimBH3 peptide for pro-survival Bcl-2-like proteins as measured by Surface Plasmon Resonance on a Biacore instrument.

| | Bcl-2 | Bcl-w | Mcl-1 | A1 | Bcl-xL |
|---|---|---|---|---|---|
| | Fold/wt BimBH3 | | | | |
| wt BimBH3 | 1 | 1 | 1 | 1 | 1 |
| A9E | 56 | 34 | 2 | 7 | 68 |
| I8A | 3 | 2 | 1 | 1 | 1 |
| L12A | 43 | 31 | 1 | 17 | 11 |
| I15A | 2 | 1 | 2 | 2 | 1 |
| G16E | 306 | >256 | 18 | 260 | 83 |
| D17A | 4 | 30 | 2 | 1 | 3 |
| F19A | 3 | 8 | 1 | 1 | 2 |
| L12A + F19A | >2273 | >513 | 1 | 120 | >1565 |

Using the data from both the phage assays and the Biacore, sequences were designing that might be specific for a particular pro-survival protein. As Mcl-1 seemed to tolerate most alanine substitutions compared to the other pro-survival proteins, it provided a target suited to testing this idea. The alanine substitutions of both L12 and F19 on Bim were combined as neither of these apparently affected binding to Mcl- 1, but had moderate effects on Bcl-$x_L$/Bcl-2 and Bcl-w binding. As predicted, a BimBH3 domain synthetic peptide incorporating both of these mutations had a dramatic detrimental effect on binding to Bcl-$x_L$, Bcl-2 and Bcl-w (>500-fold decrease in affinity) but retained essentially wild-type affinity for Mcl-1.

EXAMPLE 6

Cell Assays

The effects of various mutations within the 26 amino acid residue long BimBH3 peptides on binding to the various pro-survival proteins have thus far been tested when displayed on the surface of a phage particle or as synthetic peptides. It was therefore important to next confirm that the effects observed were reproducible when incorporated into the full-length Bim protein, and correlate the data with the biological consequences of the various mutations. Hence each of the key mutants were incorporated into a BimS expression vector which was retrovirally introduced into mammalian cells. Cell viability was then measured 30 hours after infection. Cells infected with Bim mutants that abrogated binding to pro-survival proteins would be expected to remain viable. However, mutants that do not affect binding should retain killing activity. Representative data from the killing assays are as presented in Table 7. As expected, wild-type Bim was able to kill wild-type mouse embryonic fibroblast (MEFs) cells efficiently with cell viability of 19% as measured by propidium iodide (PI) exclusion. Similarly, when the F19A mutation was incorporated into the full-length Bim protein and expressed in MEFs, this mutant protein killed cells almost as efficiently as the native Bim, which is consistent with the ability of this mutant to bind all pro-survival proteins with close to wild-type affinity. The G16E mutant, in the context of a free synthetic peptide and displayed on phage had lost significant affinity for all pro-survival proteins and this is reflected in the inability of this mutant to kill MEFs (93% cell viability). In the case of the D17A mutant, in the phage binding experiments, we could not detect any binding of this mutant when expressed on the surface of a phage particle to Bcl-$x_L$. Consistent with this result, wild-type MEFs did not appear to be killed by BimS (D17A) (89% cell viability), and this suggests that, in some cases, the binding data obtained with the phage-displayed peptides may be a more accurate reflection of their binding abilities compared to free synthetic peptides. Previous work by Willis et al. *Genes and Development* 19:1294-1305, 2005 has demonstrated that inactivation of both Mcl-1 and Bcl-$x_L$ sufficient for efficient Bak-mediated apoptosis (Willis et al. 2005 supra). Both the A9E and L12A mutants had a moderate decrease in binding affinity for Bcl-w, Bcl-2 and Bcl-$x_L$ whilst retaining near wild-type affinity for Mcl-1 and A1. This is consistent with the intermediate killing observed when these two mutants were expressed in wild-type MEFs. The abilities of the I8A and I15A mutants to kill were also tested when incorporated into the full-length Bim protein. In agreement with the phage and BIAcore results which both indicated that neither mutation effects pro-survival protein binding, these mutants were able to kill wild-type MEFs to the same degree as the native Bim protein. As control experiments, the abilities of the various mutants to kill Bax/Bak doubly-deficient MEFs were tested. As expected, none of the mutants killed these cells since Bax and Bak are required for commitment to cell death.

TABLE 7

Killing of immortalized MEFs by Bim mutants when expressed as a full-length protein (BimS) in both wild-type and Bax/Bak doubly-deficient mouse embryonic fibroblasts (MEFs).

| BimS mutants | % viability in wild-type MEFs | % viability in Bax-/-Bak-/-MEFs |
|---|---|---|
| wtBimS | 19 | 90 |
| BimS A9E | 55 | 93 |
| BimS L12A | 57 | 91 |
| BimS G16E | 93 | 97 |
| BimS D17A | 89 | 94 |
| BimS F19A | 22 | 87 |

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

BIBLIOGRAPHY

Adams et al., *Genes Dev* 17:2481-2495, 2003
Adams et al., *Nature* 318:533-538, 1985
Adams, J. M. and S. Cory *Science* 281:1322-1326, 1998
Akimaru et al., *Cytokines Mol Ther* 1:197-210, 1995
Alving et al., *Immunol Rev* 145:5-31, 1995
Bleicher et al., *Nat Rev Drug Discov* 2:369-378, 2003
Chapter 9 entitled "Peptide Synthesis" by Atherton and Shephard which is included in a publication entitled "*Synthetic Vaccines*" edited by Nicholson and published by Blackwell Scientific Publications
Chen et al. *Mol Cell* 17:393-403, 2005
Choi et al. *Oncogene* 11:1693-1698, 1995
Cory et al., *Nat Rev Cancer* 2:647-656, 2002
Cory et al., *Oncogene* 22:8590-8607, 2003
Danial and Korsmeyer, *Cell* 116:205-219, 2004
Day et al. *Cell Death and Differentiation* 6:1125-1132, 1999
*Drug Metabolism Databases and High-Throughput Testing During Drug Design and Development*, Ed Erhardt, Blackwell Science, Malden, Mass., USA, 1999
D'Sa-Eipper, C. et al. *Cancer Res.* 56:3879-3882, 1996
Egleton and Davis, *Peptides* 18:1431-1439, 1997
Erickson et al., *Science* 249:527-533, 1990
Fairlie et al. *J Biol Chem* 279:2125-2134, 2004
Fairlie et al. *Protein Expression and Purification* 26:171-178, 2002
Fix, *Pharm Res* 13:1760-1764, 1996
Glickman et al., *J Biomol Screen* 7:3-10, 2002
Hajduk et al., *J Med Chem* 42:2315-2317, 1999;
Hinds et al. *EMBO Journal* 22:1497-1507, 2003
Huang and Strasser, *Cell* 103:839-842, 2000
Johnson et al., *Peptide Turn Mimetics in Biotechnology and Pharmacy*,
Johnstone et al., *Cell* 108:153-164, 2002
Kunkel et al. *Methods Enzymol* 204:125-139, 1991
Kuntz, *Science* 257:1078-1082, 1992
Langer, *Science* 249:1527-1533, 1990
Letai et al., *Cancer Cell* 2:183-192, 2002;
Lugovskoy et al., *J Am Chem Soc* 124:1234-1240, 2002
Patton, *Nat Biotech* 16:141-143, 1998
Pellecchia et al., *Nat Rev Drug Discov* 1:211-219, 2002
Petros et al., 2000, Supra; Sattler et al., 1997, Supra
Pezzuto et al., Eds., Chapman and Hall, New York, 1993

Print et al. *Proc Natl Acad Sci USA* 95:12424-12431, 1998
Putney and Burke, *Nat Biotech* 16:153-157, 1998
Remington's Pharmaceutical Sciences, 18th Edition, Mack Publishing Company, Easton, Pa., 1990
Samanen et al., *J Pharm Pharmacol* 48:119-135, 1996
Sayani and Chien, *Crit Rev Ther Drug Carrier Syst* 13:85-184, 1996
Sidhu et al. *Methods Enzymol* 328:333-363, 2000
Strasser et al., *Nature* 348:331-333, 1990
Suntres and Shek, *J Pharm Pharmacol* 46:23-28, 1994
Szoka and Papahadjopoulos, *Ann Rev Biophys Bioeng* 9:467-508, 1980
van de Waterbeemd and Gifford, *Nat Rev Drug Disc* 2:192-204, 2003
Vaux et al., *Nature* 335:440-442, 1988
Vutla et al., *J Pharm Sci* 85:5-8, 1996
Wei et al., *Science* 292:727-730, 2001
Wells, *Methods Enzymol* 202:2699-2705, 1991
Willis et al. *Genes and Development* 19:1294-1305, 2005
Wilson-Annan et al. *Journal of Cell Biology* 162:877-888, 2003
Wohnsland et al., *J Med Chem* 44:923-930, 2001
Woodle et al., *Pharm Res* 9:260-265, 1992
Yan et al. *J Cereb Blood Flow Metab* 20:620-630, 2000
Zalipsky et al., *Bioconjug Chem* 6:705-708, 1995
Zhang, *Nat Rev Drug Discov* 1:101-102, 2002

The invention claimed is:

1. An antagonist consisting of SEQ ID NO: 1 with a substitution at only one or two amino acid residues selected from the group consisting of L12, G16, D17 and F19 of SEQ ID NO: 1, wherein said antagonist binds to Mcl-1 and shows reduced binding to other Bcl-2 proteins compared to wild type SEQ ID NO: 1, with the proviso that, when there is a substitution at only one amino acid, the substitution is not L12A or F19A.

2. The antagonist of claim 1, wherein said substitution at only two amino acid residues of SEQ ID NO: 1 consists of L12A and F19A.

3. The antagonist of claim 1 wherein said substitution at only one amino acid residue of SEQ ID NO: 1 is selected from the group consisting of L12 mutated to G, T, Q or H; D17 mutated to R; and F19 mutated to D or K; or wherein said substitutions at only two amino acid residues of SEQ ID NO: 1 are selected from the group consisting of L12 mutated to A, G, T, Q or H; D17 mutated to R; and F19 mutated to D or K.

4. The antagonist of claim 1 wherein said substitution at only one amino acid residue of SEQ ID NO: 1 is selected from the group consisting of L12Y and F19 mutated to either R, H, N or E, and wherein said substitution at only two amino acid residues of SEQ ID NO: 1 are L12Y and F19 mutated to either R, H, N or E.

5. The antagonist of claim 1, wherein when there is only one substitution, L12 is substituted with an amino acid selected from the group consisting of G, S, T, V, L, I, M, F, W, Q and H, or when there are two substitutions, L12 is substituted with an amino acid selected from the group consisting of A, G, S, T, V, L, I, M, F, W, Q and H.

6. The antagonist of claim 1, wherein when there is only one substitution, F19 is substituted with an amino acid selected from the group consisting of G, S, T, V, L, I, M, F, Y, W, D, E, N, Q, H, K and R, or when there are two substitutions, F19 is substituted with an amino acid selected from the group consisting of A, G, S, T, V, L, I, M, F, Y, W, D, E, N, Q, H, K and R.

7. The antagonist of claim 1 comprising D17A.

8. The antagonist of claim 1 comprising G16E.

9. A method of generating an antagonist according to claim 1, the method comprising the steps of:

a. mutating one or two amino acid residues selected from the group consisting of L12, G16, D17 and F19 of SEQ ID NO: 1;
b. contacting the mutated peptide with members of the pro-survival Bcl-2 family;
c. detecting the strength of binding between the mutated peptide and the pro-survival Bcl-2 family members, thereby identifying amino acid residues in the peptide of the pro-apoptotic protein associated with a binding interaction between the peptide and Mcl-1; and
d. generating an antagonist which retains binding to Mcl-1 but not to other Bcl-2 proteins contacted, wherein the antagonist binds more selectively than a wild-type sequence.

10. The method of claim 9, wherein the antagonist binds to Mcl-1.

11. The method of claim 9, wherein the antagonist binds to Mcl-1 of a cancer cell.

12. The method of claim 10 wherein the Mcl-1 is human.

13. The method of claim 11, wherein the cancer is selected from the group consisting of ABL1 protooncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and cns tumors, breast cancer, cns tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous t-cell lymphoma, dermatofi brosarcoma-protuberans, desmoplastic-small-round-cell-tumor, ductal carcinoma, endocrine cancers, endometrial cancer, ependymoma, esophageal cancer, ewing's sarcoma, extra-hepatic bile duct cancer, eye cancer, eye: melanoma, retinoblastoma, fallopian tube cancer, fanconi anaemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, rothmund-thomson syndrome, salivary gland cancer, sarcoma, schwannoma, sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer- (renal-pelvis–/– ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

* * * * *